(12) United States Patent
Blinkovsky et al.

(10) Patent No.: US 6,800,467 B1
(45) Date of Patent: Oct. 5, 2004

(54) POLYPEPTIDES HAVING AMINOPEPTIDASE ACTIVITY AND NUCLEIC ACIDS ENCODING SAME

(75) Inventors: Alexander Blinkovsky, Davis, CA (US); Kimberly Brown, Elk Grove, CA (US); Elizabeth Golightly, Davis, CA (US); Tony Byun, Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/080,127

(22) Filed: May 15, 1998

Related U.S. Application Data

(63) Continuation-in-part of application No. 08/857,886, filed on May 16, 1997.
(60) Provisional application No. 60/062,893, filed on Oct. 20, 1997.

(51) Int. Cl.[7] .................. C12N 9/00; C07K 7/00; C07K 1/00; C07K 14/00; C07K 17/00
(52) U.S. Cl. ............... 435/183; 530/300; 530/350
(58) Field of Search .................... 530/350, 402, 530/300; 536/23.2; 435/471, 70.1, 68.1, 183

(56) References Cited

U.S. PATENT DOCUMENTS 5,821,104 A * 10/1998 Holm et al.

FOREIGN PATENT DOCUMENTS

| | | |
|---|---|---|
| DE | 195 26 485 A1 | 1/1997 |
| EP | 0 384 303 | 8/1990 |
| EP | 0 480 104 A1 | 4/1992 |
| WO | WO 97/43910 | 11/1997 |
| WO | WO 96/28542 | 9/1998 |

OTHER PUBLICATIONS

Kundu et al., Applied Microbiology, Apr. 1970, pp. 598–603.*
Skolnick et al., Trends in Biotech., 18(1):34–39, 2000.*
Nakadai et al., Agr. Biol. Chem., 37(4):775–782, 1973.*
Nakadai et al., Agr. Biol. Chem., 37(4):767–774, 1973.*
Nishizawa et al., J. Biol. Chem., 269(18):13651–55, 1994.*
Jenkins et al., PCR Methods and Applications, S77–82, 1994.*
Choh, PNAS., 77(6):3211–14, 1980.*
Lazar et al, Mol.and Cell Biol 8:1247–1252, 1988.*
Burgess et al, J.Cell Bio. 111:2129–2138, 1990.*
Abstract, File Medline, Stn. Medline Ceasar Accession No. 1870 (XP–002077232), May 1977.
Abstract, File Medline, Stn Medline Caesar Accession No. 1872 (XP–002077233), Oct. 1976.
Database WPI, Section Ch, Week 9130, (XP–002077234).
Database WPI, Section Ch, Week 9710, (XP–002076623).

* cited by examiner

*Primary Examiner*—Gary Kunz
*Assistant Examiner*—Sharon Turner
(74) *Attorney, Agent, or Firm*—Robert L. Starnes

(57) ABSTRACT

The present invention relates to isolated polypeptides having aminopeptidase activity and isolated nucleic acid sequences encoding the polypeptides. The invention also relates to nucleic acid constructs, vectors, and host cells comprising the nucleic acid sequences as well as methods for producing and using the polypeptides.

30 Claims, 5 Drawing Sheets

```
ATGAGGTCGCTTTTGTGGGCTTCGTTGCTTTCGGGCGTGTTGGCTGGGAGGGCGCTTGTTTCGCCGGATGAGTTCCCCGAGGATATTCAG  90
 M  R  S  L  L  W  A  S  L  L  S  G  V  L  A  G  R  A  L  V  S  P  D  E  F  P  E  D  I  Q

TTGGAAGATCTGCTGGAAGGATCCCAACAGCTTGAGGACTTCGCCTATGCCTACCCCGAGCGCAATCGCGTCTTTGGTGGTAAAGCCCAC 180
 L  E  D  L  L  E  G  S  Q  Q  L  E  D  F  A  Y  A  Y  P  E  R  N  R  V  F  G  G  K  A  H

GACGACACGGTTAACTATCTCTACGAGGAGCTGAAGAAGACTGGCTACTATGATGTCTACAAGCAGCCTCAGGTGCACCTGTGGAGCAAT 270
 D  D  T  V  N  Y  L  Y  E  E  L  K  K  T  G  Y  Y  D  V  Y  K  Q  P  Q  V  H  L  W  S  N

GCCGACCAGACGCTCAAGGTGGGCGATGAGGAAATCGAGGCGAAGACCATGACCTACAGTCCCAGCGTCGAGGTCACCGCCGATGTAGCC 360
 A  D  Q  T  L  K  V  G  D  E  E  I  E  A  K  T  M  T  Y  S  P  S  V  E  V  T  A  D  V  A

GTCGTCAAGAACCTGGGATGCAGCGAGGCGGATTACCCATCCGATGTCGAGGGCAAGGTCGCCCTGATCAAGCGTGGAGAATGCCCGTTC 450
 V  V  K  N  L  G  C  S  E  A  D  Y  P  S  D  V  E  G  K  V  A  L  I  K  R  G  E  C  P  F

GGCGACAAGTCGGTTCTCGCTGCCAAAGCCAAGGCCGCGGCTTCGATTGTCTATAACAATGTGGCCGGATCCATGGCGGGCACCCTTGGC 540
 G  D  K  S  V  L  A  A  K  A  K  A  A  A  S  I  V  Y  N  N  V  A  G  S  M  A  G  T  L  G

GCGGCGCAGAGTGATAAGGGACCGTATTCGGCCATTGTCGGTATCAGCTTGGAGGATGGCCAGAAGCTGATCAAGCTTGCTGAGGCTGGA 630
 A  A  Q  S  D  K  G  P  Y  S  A  I  V  G  I  S  L  E  D  G  Q  K  L  I  K  L  A  E  A  G

TCGGTATCTGTGGATCTGTGGGTGGATAGTAAGCAGGAGAACCGTACGACGTATAACGTTGTCGCGCAGACGAAGGGCGGCGATCCGAAC 720
 S  V  S  V  D  L  W  V  D  S  K  Q  E  N  R  T  T  Y  N  V  V  A  Q  T  K  G  G  D  P  N

AACGTCGTCGCGCTGGGTGGCCACACGGACTCAGTCGAGGCGGGCCCTGGTATCAACGACGATGGCTCGGGCATTATTAGCAACTTGGTC 810
 N  V  V  A  L  G  G  H  T  D  S  V  E  A  G  P  G  I  N  D  D  G  S  G  I  I  S  N  L  V

ATTGCCAAAGCGCTCACGCAGTACTCCGTCAAGAATGCCGTGCGCTTCCTCTTCTGGACAGCAGAGGAGTTCGGTCTGCTGGGCAGCAAC 900
 I  A  K  A  L  T  Q  Y  S  V  K  N  A  V  R  F  L  F  W  T  A  E  E  F  G  L  L  G  S  N

TACTACGTCTCCCATCTGAATGCCACCGAGCTGAACAAGATCCGACTGTACCTGAACTTCGACATGATCGCCTCACCTAACTACGCCCTC 990
 Y  Y  V  S  H  L  N  A  T  E  L  N  K  I  R  L  Y  L  N  F  D  M  I  A  S  P  N  Y  A  L

ATGATCTATGACGGTGATGGATCGGCGTTCAACCAGAGCGGACCGGCCGGTTCCGCCCAGATCGAGAAACTGTTCGAGGACTACTACGAC 1080
 M  I  Y  D  G  D  G  S  A  F  N  Q  S  G  P  A  G  S  A  Q  I  E  K  L  F  E  D  Y  Y  D

TCCATCGACCTGCCTCATATCCCCACCCAGTTTGACGGACGTTCCGACTACGAGGCCTTTATCCTGAACGGCATTCCGTCCGGTGGACTC 1170
 S  I  D  L  P  H  I  P  T  Q  F  D  G  R  S  D  Y  E  A  F  I  L  N  G  I  P  S  G  G  L

TTCACGGGCGCCGAGGGCATCATGTCCGAAGAGAACGCAAGCCGCTGGGGAGGTCAAGCCGGCGTGGCCTACGACGCCAACTACCACGCC 1260
 F  T  G  A  E  G  I  M  S  E  E  N  A  S  R  W  G  G  Q  A  G  V  A  Y  D  A  N  Y  H  A

GCGGGAGACAACATGACCAACCTCAACCATGAAGCCTTCCTGATCAACTCCAAAGCCACCGCCTTCGCCGTCGCCACCTACGCCAACGAC 1350
 A  G  D  N  M  T  N  L  N  H  E  A  F  L  I  N  S  K  A  T  A  F  A  V  A  T  Y  A  N  D

CTCTCCTCGATCCCCAAACGGAATACCACATCCTCCTTGCACCGACGAGCCCGCACCATGCGACCATTCGGCAAGAGAGCTCCGAAGACA 1440
 L  S  S  I  P  K  R  N  T  T  S  S  L  H  R  R  A  R  T  M  R  P  F  G  K  R  A  P  K  T

CACGCTCACGTATCAGGATCCGGATGCTGGCATTCTCAAGTCGAGGCATAG 1491
 H  A  H  V  S  G  S  G  C  W  H  S  Q  V  E  A  .
```

Fig. 1

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 1491 base pairs
       (B) TYPE: nucleic acid
       (C) STRANDEDNESS: single
       (D) TOPOLOGY: linear (ix) FEATURE:

(xi) SEQUENCE DESCRIPTION: SEQ ID NO:1:

```
ATGAGGTCGC TTTTGTGGGC TTCGTTGCTT TCGGGCGTGT TGGCTGGGAG GGCGCTTGTT      60

TCGCCGGATG AGTTCCCCGA GGATATTCAG TTGGAAGATC TGCTGGAAGG ATCCCAACAG     120

CTTGAGGACT TCGCCTATGC CTACCCCGAG CGCAATCGCG TCTTTGGTGG TAAAGCCCAC     180

GACGACACGG TTAACTATCT CTACGAGGAG CTGAAGAAGA CTGGCTACTA TGATGTCTAC     240

AAGCAGCCTC AGGTGCACCT GTGGAGCAAT GCCGACCAGA CGCTCAAGGT GGGCGATGAG     300

GAAATCGAGG CGAAGACCAT GACCTACAGT CCCAGCGTCG AGGTCACCGC CGATGTAGCC     360

GTCGTCAAGA ACCTGGGATG CAGCGAGGCG GATTACCCAT CCGATGTCGA GGGCAAGGTC     420

GCCCTGATCA AGCGTGGAGA ATGCCCGTTC GGCGACAAGT CGGTTCTCGC TGCCAAAGCC     480

AAGGCCGCGG CTTCGATTGT CTATAACAAT GTGGCCGGAT CCATGGCGGG CACCCTTGGC     540

GCGGCGCAGA GTGATAAGGG ACCGTATTCG GCCATTGTCG GTATCAGCTT GGAGGATGGC     600

CAGAAGCTGA TCAAGCTTGC TGAGGCTGGA TCGGTATCTG TGGATCTGTG GGTGGATAGT     660

AAGCAGGAGA ACCGTACGAC GTATAACGTT GTCGCGCAGA CGAAGGGCGG CGATCCGAAC     720

AACGTCGTCG CGCTGGGTGG CCACACGGAC TCAGTCGAGG CGGGCCCTGG TATCAACGAC     780

GATGGCTCGG GCATTATTAG CAACTTGGTC ATTGCCAAAG CGCTCACGCA GTACTCCGTC     840

AAGAATGCCG TGCGCTTCCT CTTCTGGACA GCAGAGGAGT TCGGTCTGCT GGGCAGCAAC     900

TACTACGTCT CCCATCTGAA TGCCACCGAG CTGAACAAGA TCCGACTGTA CCTGAACTTC     960

GACATGATCG CCTCACCTAA CTACGCCCTC ATGATCTATG ACGGTGATGG ATCGGCGTTC    1020

AACCAGAGCG GACCGGCCGG TTCCGCCCAG ATCGAGAAAC TGTTCGAGGA CTACTACGAC    1080

TCCATCGACC TGCCTCATAT CCCCACCCAG TTTGACGGAC GTTCCGACTA CGAGGCCTTT    1140

ATCCTGAACG GCATTCCGTC CGGTGGACTC TTCACGGGCG CCGAGGGCAT CATGTCCGAA    1200

GAGAACGCAA GCCGCTGGGG AGGTCAAGCC GGCGTGGCCT ACGACGCCAA CTACCACGCC    1260

GCGGGAGACA ACATGACCAA CCTCAACCAT GAAGCCTTCC TGATCAACTC CAAAGCCACC    1320

GCCTTCGCCG TCGCCACCTA CGCCAACGAC CTCTCCTCGA TCCCCAAACG GAATACCACA    1380

TCCTCCTTGC ACCGACGAGC CCGCACCATG CGACCATTCG GCAAGAGAGC TCCGAAGACA    1440

CACGCTCACG TATCAGGATC CGGATGCTGG CATTCTCAAG TCGAGGCATA G            1491
```

(2) INFORMATION FOR SEQ ID NO:2:

(i) SEQUENCE CHARACTERISTICS:
       (A) LENGTH: 496 amino acids
       (B) TYPE: amino acid
       (C) STRANDEDNESS: single
       (D) TOPOLOGY: linear (xi) SEQUENCE DESCRIPTION: SEQ ID NO:2:

```
Met Arg Ser Leu Leu Trp Ala Ser Leu Leu Ser Gly Val Leu Ala Gly
 1               5                  10                  15

Arg Ala Leu Val Ser Pro Asp Glu Phe Pro Glu Asp Ile Gln Leu Glu
            20                  25                  30

Asp Leu Glu Gly Ser Gln Gln Leu Glu Asp Phe Ala Tyr Ala Tyr
        35                  40                  45

Pro Glu Arg Asn Arg Val Phe Gly Gly Lys Ala His Asp Asp Thr Val
    50                  55                  60

Asn Tyr Leu Tyr Glu Glu Leu Lys Lys Thr Gly Tyr Tyr Asp Val Tyr
65                  70                  75                  80

Lys Gln Pro Gln Val His Leu Trp Ser Asn Ala Asp Gln Thr Leu Lys
                85                  90                  95

Val Gly Asp Glu Glu Ile Glu Ala Lys Thr Met Thr Tyr Ser Pro Ser
            100                 105                 110

Val Glu Val Thr Ala Asp Val Ala Val Lys Asn Leu Gly Cys Ser
            115                 120                 125

Glu Ala Asp Tyr Pro Ser Asp Val Glu Gly Lys Val Ala Leu Ile Lys
    130                 135                 140

Arg Gly Glu Cys Pro Phe Gly Asp Lys Ser Val Leu Ala Ala Lys Ala
145                 150                 155                 160

Lys Ala Ala Ser Ile Val Tyr Asn Asn Val Ala Gly Ser Met Ala
                165                 170                 175

Gly Thr Leu Gly Ala Ala Gln Ser Asp Lys Gly Pro Tyr Ser Ala Ile
            180                 185                 190

Val Gly Ile Ser Leu Glu Asp Gly Gln Lys Leu Ile Lys Leu Ala Glu
            195                 200                 205

Ala Gly Ser Val Ser Val Asp Leu Trp Val Asp Ser Lys Gln Glu Asn
    210                 215                 220

Arg Thr Thr Tyr Asn Val Val Ala Gln Thr Lys Gly Gly Asp Pro Asn
225                 230                 235                 240

Asn Val Val Ala Leu Gly Gly His Thr Asp Ser Val Glu Ala Gly Pro
                245                 250                 255

Gly Ile Asn Asp Asp Gly Ser Gly Ile Ile Ser Asn Leu Val Ile Ala
            260                 265                 270

Lys Ala Leu Thr Gln Tyr Ser Val Lys Asn Ala Val Arg Phe Leu Phe
            275                 280                 285

Trp Thr Ala Glu Glu Phe Gly Leu Leu Gly Ser Asn Tyr Tyr Val Ser
    290                 295                 300

His Leu Asn Ala Thr Glu Leu Asn Lys Ile Arg Leu Tyr Leu Asn Phe
305                 310                 315                 320

Asp Met Ile Ala Ser Pro Asn Tyr Ala Leu Met Ile Tyr Asp Gly Asp
                325                 330                 335

Gly Ser Ala Phe Asn Gln Ser Gly Pro Ala Gly Ser Ala Gln Ile Glu
            340                 345                 350

Lys Leu Phe Glu Asp Tyr Tyr Asp Ser Ile Asp Leu Pro His Ile Pro
            355                 360                 365

Thr Gln Phe Asp Gly Arg Ser Asp Tyr Glu Ala Phe Ile Leu Asn Gly
    370                 375                 380

Ile Pro Ser Gly Gly Leu Phe Thr Gly Ala Glu Gly Ile Met Ser Glu
385                 390                 395                 400

Glu Asn Ala Ser Arg Trp Gly Gly Gln Ala Gly Val Ala Tyr Asp Ala
                405                 410                 415
```

```
Asn Tyr His Ala Ala Gly Asp Asn Met Thr Asn Leu Asn His Glu Ala
            420                 425                 430

Phe Leu Ile Asn Ser Lys Ala Thr Ala Phe Ala Val Ala Thr Tyr Ala
            435                 440                 445

Asn Asp Leu Ser Ser Ile Pro Lys Arg Asn Thr Thr Ser Ser Leu His
            450                 455                 460

Arg Arg Ala Arg Thr Met Arg Pro Phe Gly Lys Arg Ala Pro Lys Thr
465                 470                 475                 480

His Ala His Val Ser Gly Ser Gly Cys Trp His Ser Gln Val Glu Ala
                485                 490                 495

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

Cys Cys Ile Gly Ala Tyr Gly Ala Arg Thr Thr Tyr Cys Cys Ile Gly
1               5                   10                  15

Ala Arg Gly Ala
            20

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

Arg Thr Thr Tyr Thr Thr Ile Ala Cys Ile Ala Cys Ile Gly Cys Ile
1               5                   10                  15

Ala Cys Arg Thr Cys Ile Gly Cys Ile Gly Thr Ile Ala Cys Tyr Thr
            20                  25                  30

Cys Ile Ala Cys
            35

(2) INFORMATION FOR SEQ ID NO:5:

(i) SEQUENCE CHARACTERISTICS:
        (A) LENGTH: 537 amino acids
        (B) TYPE: amino acid
        (C) STRANDEDNESS: single
        (D) TOPOLOGY: linear (xi) SEQUENCE DESCRIPTION: SEQ ID NO:5:

Met His Phe Ser Leu Lys Gln Leu Ala Val Ala Ala Phe Tyr Ala Thr
1               5                   10                  15

Asn Leu Gly Ser Ala Tyr Val Ile Pro Gln Phe Phe Gln Glu Ala Phe
            20                  25                  30

Gln Gln Glu Glu Pro Ile Glu Asn Tyr Leu Pro Gln Leu Asn Asp Asp
            35                  40                  45

Asp Ser Ser Ala Val Ala Ala Asn Ile Pro Lys Pro His Ile Pro Tyr
    50                  55                  60
```

-continued

```
Phe Met Lys Pro His Val Glu Ser Glu Lys Leu Gln Asp Lys Ile Lys
 65                  70                  75                  80

Val Asp Asp Leu Asn Ala Thr Ala Trp Asp Leu Tyr Arg Leu Ala Asn
                 85                  90                  95

Tyr Ser Thr Pro Asp Tyr Gly His Pro Thr Arg Val Ile Gly Ser Lys
            100                 105                 110

Gly His Asn Lys Thr Met Glu Tyr Ile Leu Asn Val Phe Asp Asp Met
        115                 120                 125

Gln Asp Tyr Tyr Asp Val Ser Leu Gln Glu Phe Glu Ala Leu Ser Gly
    130                 135                 140

Lys Ile Ile Ser Phe Asn Leu Ser Asp Ala Glu Thr Gly Lys Ser Phe
145                 150                 155                 160

Ala Asn Thr Thr Ala Phe Ala Leu Ser Pro Val Asp Gly Phe Val
                165                 170                 175

Gly Lys Leu Val Glu Ile Pro Asn Leu Gly Cys Glu Glu Lys Asp Tyr
                180                 185                 190

Ala Ser Val Val Pro Pro Arg His Asn Glu Lys Gln Ile Ala Leu Ile
                195                 200                 205

Glu Arg Gly Lys Cys Pro Phe Gly Asp Lys Ser Asn Leu Ala Gly Lys
    210                 215                 220

Phe Gly Phe Thr Ala Val Val Ile Tyr Asp Asn Glu Pro Lys Ser Lys
225                 230                 235                 240

Glu Gly Leu His Gly Thr Leu Gly Glu Pro Thr Lys His Thr Val Ala
                245                 250                 255

Thr Val Gly Val Pro Tyr Lys Val Gly Lys Lys Leu Ile Ala Asn Ile
                260                 265                 270

Ala Leu Asn Ile Asp Tyr Ser Leu Tyr Phe Ala Met Asp Ser Tyr Val
                275                 280                 285

Glu Phe Ile Lys Thr Gln Asn Ile Ile Ala Asp Thr Lys His Gly Asp
    290                 295                 300

Pro Asp Asn Ile Val Ala Leu Gly Ala His Ser Asp Ser Val Glu Glu
305                 310                 315                 320

Gly Pro Gly Ile Asn Asp Asp Gly Ser Gly Thr Ile Ser Leu Leu Asn
                325                 330                 335

Val Ala Lys Gln Leu Thr His Phe Lys Ile Asn Asn Lys Val Arg Phe
                340                 345                 350

Ala Trp Trp Ala Ala Glu Glu Glu Gly Leu Leu Gly Ser Asn Phe Tyr
                355                 360                 365

Ala Tyr Asn Leu Thr Lys Glu Glu Asn Ser Lys Ile Arg Val Phe Met
                370                 375                 380

Asp Tyr Asp Met Met Ala Ser Pro Asn Tyr Glu Tyr Glu Ile Tyr Asp
385                 390                 395                 400

Ala Asn Asn Lys Glu Asn Pro Lys Gly Ser Glu Glu Leu Lys Asn Leu
                405                 410                 415

Tyr Val Asp Tyr Tyr Lys Ala His His Leu Asn Tyr Thr Leu Val Pro
                420                 425                 430

Phe Asp Gly Arg Ser Asp Tyr Val Gly Phe Ile Asn Asn Gly Ile Pro
                435                 440                 445

Ala Gly Gly Ile Ala Thr Gly Ala Glu Lys Asn Asn Val Asn Asn Gly
                450                 455                 460

Lys Val Leu Asp Arg Cys Tyr His Gln Leu Cys Asp Asp Val Ser Asn
465                 470                 475                 480
```

```
Leu Ser Trp Asp Ala Phe Ile Thr Asn Thr Lys Leu Ile Ala His Ser
                485                 490                 495

Val Ala Thr Tyr Ala Asp Ser Phe Glu Gly Phe Pro Lys Arg Glu Thr
            500                 505                 510

Gln Lys His Lys Glu Val Asp Ile Leu Asn Ala Gln Gln Pro Gln Phe
        515                 520                 525

Lys Tyr Arg Ala Asp Phe Leu Ile Ile
    530                 535

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

ATGATGAGGT CGCTTTTGTG GGC                                            23

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:7:

GGGATGCATC TATGCCTCGA CTT                                            23

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:8:

ATTTAAATCA CCATGAGGTC GCTTTTGTGG GC                                  32

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GGGTTAATTA ACTATGCCTC GACTTGAGAA TG                                  32
```

POLYPEPTIDES HAVING AMINOPEPTIDASE ACTIVITY AND NUCLEIC ACIDS ENCODING SAME

CROSS-REFERENCE TO RELATED APPLICATIONS

This application is a continuation-in-part of pending U.S. application Ser. No. 08/857,886 filed on May 16, 1997, and pending provisional U.S. application Serial No. 60/062,893 filed on Oct. 20, 1997, which applications are fully incorporated herein by reference.

BACKGROUND OF THE INVENTION

1. Field of the Invention

The present invention relates to polypeptides having aninopeptidase activity and isolated nucleic acid sequences encoding the polypeptides. The invention also relates to nucleic acid constructs, vectors, and host cells comprising the nucleic acid sequences as well as methods for producing the polypeptides. The present invention further relates to methods of obtaining protein hydrolysates useful as flavour improving agents.

2. Description of the Related Art

Various food products, e.g., soups, sauces and seasonings, contain flavoring agents obtained by hydrolysis of proteinaceous materials. This hydrolysis is conventionally accomplished using strong hydrochloric acid, followed by neutralization with sodium hydroxide. However, such chemical hydrolysis leads to severe degradation of the amino acids obtained during the hydrolysis, and also to hazardous byproducts formed in the course of this chemical reaction. Increasing concern over the use of flavoring agents obtained by chemical hydrolysis has led to the development of enzymatic hydrolysis processes.

Enzymatic hydrolysis processes of proteinaceous materials aim at obtaining a high degree of hydrolysis (DH), and this is usually attained using a complex of unspecific acting proteolytic enzymes (i.e., unspecific-acting endo- and exo-peptidases). For example, WO 94/25580 describes a method for hydrolyzing proteins by use of an unspecific acting enzyme preparation obtained from *Aspergillus oryzae*. Specific acting proteolytic enzymes have not been used for this purpose because such enzymes only lead to an inadequate degree of hydrolysis.

Polypeptides having aminopeptidase activity catalyze the removal of one or more amino acid residues from the N-terminus of peptides, polypeptides, and proteins. Such polypeptides are classified under the Enzyme Classification Number E.C. 3.4.11.- of the International Union of Biochemistry and Molecular Biology.

WO 96/28542 discloses an aminopeptidase which has a moleculer weight of 35 kDa. JP-7-5034631 (Noda) discloses a leucine aminopeptidase obtained from yellow koji mold, which includes *Aspergillus oryzae*. JP-7-4021798 (Zaidan Hojin Noda Sangyo) discloses the production of miso by adding a leucine aminopeptidase II prepared by cultivating a number of strains, including *Aspergillus oryzae* strain 460 (ATCC 20386) and strain IAM 2616. *Aspergillus oryzae* strain 460 is known to produce a number of leucine aminopeptidases of which three have a molecular weight of 26.5, 56, and 61 kDa by gel filtration (Nakada et al., 1972, *Agricultural and Biological Chemistry* 37: 757–765; Nakada et al., 1972, *Agricultural and Biological Chemistry* 37: 767–774; and Nakada et al., 1972, *Agricultural and Biological Chemistry* 37: 775–782; respectively). *Penicilium citrium* produces an intracellular leucine aminopeptidase with a molecular weight of 65 kDa by SDS-PAGE (Kwon et al., 1996, *Journal of Industrial Microbiology* 17: 30–35).

WO 97/04108 (Roehm) discloses DNA encoding an *Aspergillus sojae*leucine aminopeptidase. Chang and Smith (1989, *Journal of Biological Chemistry* 264: 6979–6983) disclose the molecular cloning and sequencing of a gene encoding a vacuolar aminopeptidase from *Saccharomyces cerevisiae*. Chang et al. (1992, *Journal of Biological Chemistry* 267: 8007–8011) disclose the molecular cloning and sequencing of a gene encoding a methionine aminopeptidase from *Saccharomyces cerevisiae*.

So The production of protein hydrolysates with desirable organoleptic properties and high degrees of hydrolysis generally requires the use of a mixture of peptidase activities. It would be desirable to provide a single component peptidase enzyme which has activity useful for improving the organoleptic properties and degree of hydrolysis of protein hydrolysates used in food products either alone or in combination with other enzymes.

It is an object of the present invention to provide improved polypeptides having aminopeptidase activity as well as methods for obtaining protein hydrolysates with desirable organoleptic qualities and high degrees of hydrolysis.

SUMMARY OF THE INVENTION

The present invention relates to isolated polypeptides having aminopeptidase activity selected from the group consisting of:

(a) a polypeptide having an amino acid sequence which has at least 50% identity with the amino acid sequence of SEQ ID NO:2;

(b) a polypeptide encoded by a nucleic acid sequence which hybridizes under medium stringency conditions with (i) the nucleic acid sequence of SEQ ID NO:1, (ii) its complementary strand, or (iii) a subsequence thereof;

(c) an allelic variant of (a) or (b); and (d) a fragment of (a), (b), or (c), wherein the fragment has aminopeptidase activity; and (e) a polypeptide having aminopeptidase activity with physicochemical properties of (i) a pH optimum in the range of from about pH 7.27 to about pH 10.95 determined at ambient temperature in the presence of Ala-para-nitroanilide; (ii) a temperature stability of 90% or more, relative to initial activity, at pH 7.5 determined after incubation for 20 minutes at 60° C. in the absence of substrate; and (iii) an activity towards Xaa-para-nitroanilide wherein Xaa is selected from the group consisting of Leu, Glu, Gly, Ala, and Pro.

The present invention also relates to isolated nucleic acid sequences encoding the polypeptides and to nucleic acid constructs, vectors, and host cells comprising the nucleic acid sequences as well as methods for producing the polypeptides.

The present invention also relates to methods for obtaining hydrolysates from proteinaceous substrates which comprise subjecting the proteinaceous material to a polypeptide with aminopeptidase activity alone or in combination with an endopeptidase, and to hydrolysates obtained from the method.

The present invention also relates to methods for obtaining from a proteinaceous substrate a hydrolysate enriched in free glutamic acid and/or peptide bound glutamic acid residues, which methods comprise subjecting the substrate to a deamidation process and to the action of a polypeptide having aminopeptidase activity.

The present invention further relates to flavor-improving compositions comprising a polypeptide with aminopeptidase activity. The compositions may further comprise additional enzymatic activities.

In a final aspect, the methods of the invention may be used in food related applications to improve flavor, such as baking. Alternatively, flavor improvement in foods may be achieved by the addition of hydrolysates obtained by the methods of the invention.

BRIEF DESCRIPTION OF THE FIGURES

FIG. 1 shows the nucleic acid sequence and the deduced amino acid sequence of an *Aspergillus oryzae* ATCC 20386 aminopeptidase (SEQ ID NOS: 1 and 2, respectively).

DETAILED DESCRIPTION OF THE INVENTION

Polypeptides Having Aminopeptidase Activity

Figure 2:
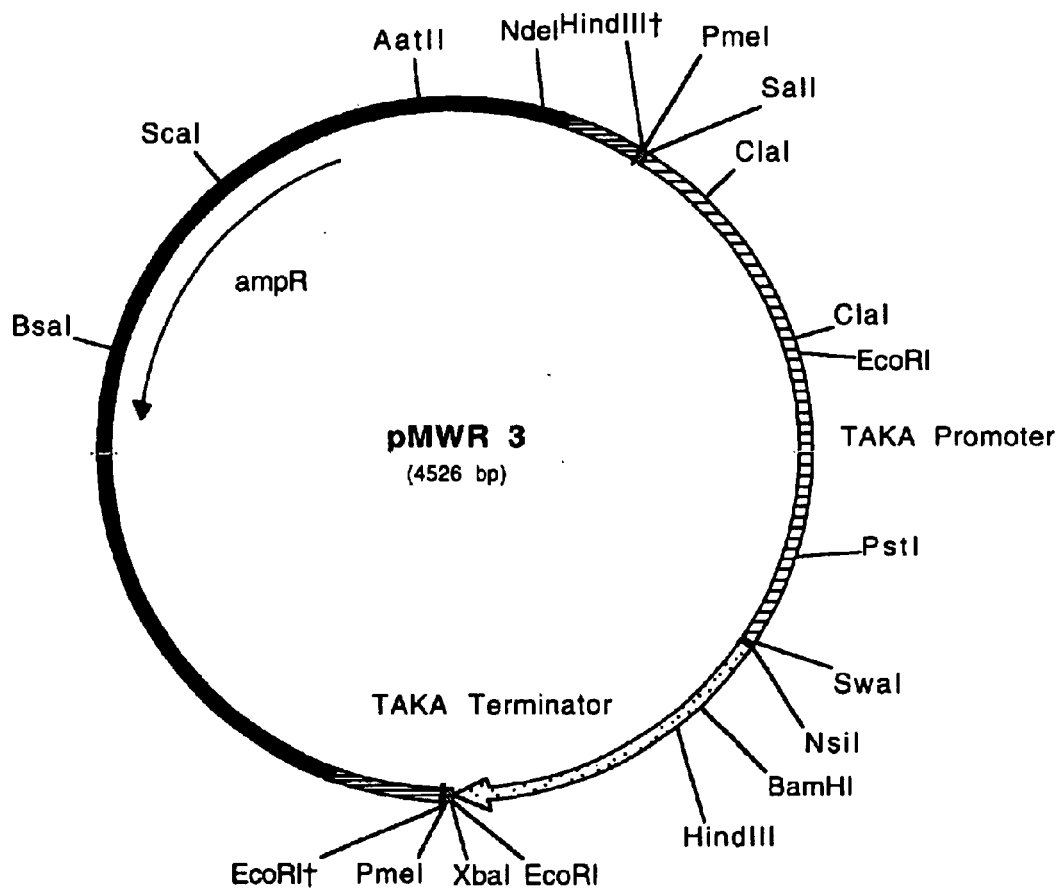
FIG. 2 shows a restriction map of pMWR3.

The term "aminopeptidase activity" is defined herein as a peptidase activity which catalyzes the removal of amino acids from the N-terminal end of peptides, oligopeptides or proteins. Defined in a general manner, the aminopeptidase activity is capable of cleaving the amino acid X from the N-terminus of a peptide, polypeptide, or protein, wherein X may represent any amino acid residue selected from the group consisting of Ala, Arg, Asn, Asp, Cys, Gln, Glu, Gly, His, Ile, Leu, Lys, Met, Phe, Pro, Ser, Thr, Trp, Tyr, and Val, but at least Leu, Glu, Gly, Ala, and/or Pro. It will be understood that the isolated polypeptides having aminopeptidase activity of the present invention may be unspecific as to the amino acid sequence of the peptide, polypeptide, or protein to be cleaved.

In a first embodiment, the present invention relates to isolated polypeptides having an amino acid sequence which has a degree of identity. to the amino acid sequence of SEQ ID NO:2 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of identity between two amino acid sequences is determined by the Clustal method (Higgins, 1989, *CABIOS* 5: 151–153) with an identity table, a gap penalty of 10, and a gap length penalty of 10.

Preferably, the polypeptides of the present invention comprise the amino acid sequence of SEQ ID NO:2 or an allelic variant; and a fragment thereof, wherein the fragment has aminopeptidase activity. In a more preferred embodiment, the polypeptides of the present invention comprise the amino acid sequence of SEQ ID NO:2. In another preferred embodiment, the polypeptide of the present invention has the amino acid sequence of SEQ ID NO:2 or a fragment thereof, wherein the fragment has aminopeptidase activity. A fragment of SEQ ID NO:2 is a polypeptide having one or more amino acids deleted from the amino and/or carboxy terminus of this amino acid sequence. In a most preferred embodiment, the polypeptide has the amino acid sequence of SEQ ID NO:2.

Preferably, a fragment contains at least 330 amino acid residues, more preferably at least 380 amino acid residues, and most preferably at least 430 amino acid residues.

An allelic variant denotes any of two or more alternative forms of a gene occupying the same chomosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant is also used to denote a protein encoded by an allelic variant of a gene.

The amino acid sequences of the homologous polypeptides may differ from the amino acid sequence of SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated polypeptides having aminopeptidase activity which are encoded by nucleic acid sequences which hybridize under low stringency conditions, more preferably medium stringency conditions, and most preferably high stringency conditions, with an oligonucleotide probe which hybridizes under the same conditions with the nucleic acid sequence of SEQ ID NO:1 or its complementary strand (J. Sambrook, E. F. Fritsch, and T. Maniatis, 1989, *Molecular Cloning, A Laboratory Manual,* 2d edition, Cold Spring Harbor, N.Y.); or allelic variants and fragments of the polypeptides, wherein the fragments have aminopeptidase activity.

Hybridization indicates that the nucleic acid sequence hybridizes to the oligonucleotide probe corresponding to the polypeptide encoding part of the nucleic acid sequence shown in SEQ ID NO:1, under low to high stringency conditions (i.e., prehybridization and hybridization at 42° C. in 5×SSPE, 0.3% SDS, 200 µg/ml sheared and denatured salmon sperm DNA, and either 25, 35 or 50% formamide for low, medium and high stringencies, respectively), following standard Southern blotting procedures.

The amino acid sequence of SEQ ID NO:2 or a partial sequence thereof may be used to design an oligonucleotide probe, or a nucleic acid sequence encoding a polypeptide of the present invention, such as the nucleic acid sequence of SEQ ID NO:1, or a subsequence thereof, may be used to identify and clone DNA encoding polypeptides having aminopeptidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin).

Thus, a genomic, cDNA or combinatorial chemical library prepared from such other organisms may be screened for DNA which hybridizes with the probes described above and which encodes a polypeptide having aninopeptidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1, the carrier material is used in a Southern blot in which the carrier material is finally washed three times for 30 minutes each using 2×SSC, 0.2% SDS preferably at least 50° C., more preferably at least 55° C., more preferably at least 60° C., more preferably at least 65° C., even more preferably at least 70° C., and most preferably at least 75° C. Molecules to which the oligonucleotide probe hybridizes under these conditions are detected using X-ray film.

In a third embodiment, the present invention relates to isolated polypeptides having the following physicochemical properties: (a) a pH optimum in the range of from about pH 7.27 to about pH 10.95 determined at ambient temperature in the presence of Ala-para-nitroanilide; (ii) a temperature stability of 90% or more, relative to initial activity, at pH 7.5 determined after incubation for 20 minutes at 60° C. in the absence of substrate; and (iii) an activity towards Xaa-para-nitroanilide wherein Xaa is selected from the group consisting of Leu, Glu, Gly, Ala, and Pro. The polypeptides of the present invention also have the ability to hydrolyze other substrates.

In a preferred embodiment, the pH optimum in the range of from about pH 7.27 to about pH 10.95, more preferably in the range of from about pH 8.03 to about pH 10.95, and most preferably in the range of from about pH 8.62 to about pH 10.51 determined after incubation for 5 minutes at ambient temperature in the presence of Ala-Pro-para-nitroanilide.

In a fourth embodiment, the present invention relates to isolated polypeptides having immunochemical identity or partial immunochemical identity to the polypeptide having the amino acid sequence of SEQ ID NO:2. The immunochemical properties are determined by immunological cross-reaction identity tests by the well-known Ouchterlony double immunodiffusion procedure. Specifically, an antiserum containing antibodies which are immunoreactive or bind to epitopes of the polypeptide having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Kroll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

Polypeptides encoded by nucleic acid sequences which hybridize with an oligonucleotide probe which hybridizes with the nucleic acid sequence of SEQ ID NO:1, its complementary strand, or allelic variants and subsequences of SEQ ID NO:1; allelic variants and fragments of the polypeptides; or the homologous polypeptides and polypeptides having identical or partially identical immunological properties may be obtained from microorganisms of any genus.

In a preferred embodiment, these polypeptides may be obtained from a bacterial source. For example, these polypeptides may be obtained from a gram positive bacterium such as a Bacillus strain, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis*; or a Streptomyces strain, e.g., *Streptomyces lividans* or *Streptomyces murinus*; or from a gram negative bacterium, e.g., *E. coli* or Pseudomonas sp.

The polypeptides may be obtained from a fungal source, and more preferably from a yeast strain such as a Candida, Kluyveromyces, Pichia, Saccharomyces, Schizosaccharomyces, or Yarrowia strain; or a filamentous fungal strain such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma strain.

In a preferred embodiment, the polypeptides are obtained from a *Saccharomyces cartsbergensis, Saccharomyces cerevisiae, Saccharomyces diastaticus, Saccharomyces douglasii, Saccharomyces kluyveri, Saccharomyces norbensis* or *Saccharomyces oviformis*strain.

In another preferred embodiment, the polypeptides are obtained from a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium*

*sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderna viride* strain.

The polypeptides of the present invention are preferably obtained from species of Aspergillus including, but not limited to, *Aspergillus aculeatus, Aspergillus awamori, Aspergillus foetidus, Aspergillus japonicus, Aspergillus nidulans, Aspergillus niger,* or *Aspergillus oryzae.*

In a more preferred embodiment, a polypeptide of the present invention is obtained from an *Aspergillus oryzae* strain, and most preferably from *Aspergillus oryzae* ATCC 20386 or a mutant strain thereof, e.g., the polypeptide with the amino acid sequence of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. The polypeptides of the present invention may also be obtained from microorganisms which are synonyms of Aspergillus as defined by Raper, K. D. and Fennel, D. I., 1965, *The Genus Aspergillus,* The Wilkins Company, Baltimore. Aspergilli are mitosporic fungi characterized by an aspergillum comprised of a conidiospore stipe with no known teleomorphic states terminating in a vesicle, which in turn bears one or two layers of synchronously formed specialized cells, variously referred to as sterigmata or phialides, and asexually formed spores referred to as conidia Known teleomorphs of Aspergillus include Eurotium, Neosartorya, and Emericella. Strains of Aspergillus and teleomorphs thereof are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding the polypeptide has been detected with the probe(s), the sequence may be isolated or cloned by utilizing techniques which are known to those of ordinary skill in the art (see, e.g., Sambrook et al., 1989, supra).

For purposes of the present invention, the term "obtained from" as used herein in connection with a given source shall mean that the polypeptide is produced by the source or by a cell in which a gene from the source has been inserted.

As defined herein, an "isolated" polypeptide is a polypeptide which is essentially free of other non-aminopeptidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Nucleic Acid Sequences

The present invention also relates to isolated nucleic acid sequences which encode a polypeptide of the present invention. In a preferred embodiment, the nucleic acid sequence encodes a polypeptide obtained from Aspergillus, e.g., *Aspergillus oryzae,* and in a more preferred embodiment, the nucleic acid sequence is obtained from *Aspergillus oryzae* ATCC 20386, e.g., the nucleic acid sequence of SEQ ID NO:1. In another more preferred embodiment, the nucleic acid sequence is the sequence contained in plasmid pEJG18 which is contained in *Escherichia coli* NRRL B-21677. The present invention also encompasses nucleic acid sequences which encode a polypeptide having the amino acid sequence of SEQ ID NO:2, which differ from SEQ ID NO:1 by virtue of the degeneracy of the genetic code. The present invention also relates to subsequences of SEQ ID NO:1 which encode fragments of SEQ ID NO:2 which have aminopeptidase activity. A subsequence of SEQ ID NO:1 is a nucleic acid sequence encompassed by SEQ ID NO:1 except that one or more nucleotides from the 5' end and/or 3' end have been deleted. Preferably, a subsequence contains at least 990 nucleotides, more preferably at least 1140 nucleotides, and most preferably at least 1290 nucleotides.

The nucleic acid sequences may be obtained from microorganisms which are taxonomic equivalents of Aspergillus as defined by Raper, K. D. and Fennel, D. I., 1965, supra., regardless of the species name by which they are known.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Aspergillus, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the nucleic acid sequence of SEQ ID NO:1 of at least about 50%, preferably about 60%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Clustal method (Higgins, 1989, supra) with an identity table, a gap penalty of 10, and a gap length penalty of 10.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for aminopeptidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

The present invention also relates to isolated nucleic acid sequences encoding a polypeptide of the present invention, which hybridize under low stringency conditions, more preferably medium stringency conditions, and most preferably high stringency conditions, with an oligonucleotide probe which hybridizes under the same conditions with the nucleic acid sequence of SEQ ID NO:1 or its complementary strand; or allelic variants and subsequences thereof (Sambrook et al., 1989, supra).

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the production of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide.

The promoter may be any nucleic acid sequence which shows transcriptional activity in the host cell of choice including mutant, truncated, and hybrid promoters, and may be obtained from genes encoding extacellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (U.S. Pat. No. 4,288,627), and mutant, truncated, and hybrid promoters thereof. Particularly preferred promoters for use in filamentous fungal host cells are the TAKA amylase, NA2-tpi (a hybrid of the promoters from the genes encoding *Aspergillus niger* neutral alpha-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423–488. In a mammalian host cell, useful promoters include viral promoters such as those from Simian Virus 40 (SV40), Rous sarcoma virus (RSV), adenovirus, bovine papilloma virus (BPV), and human cytomegalovirus (CMV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15: 5983–5990. Polyadenylation sequences are well known in the art for mammalian host cells.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. The signal peptide coding region may be obtained from a glucoamylase or an amylase gene from an Aspergillus species, a lipase or proteinase gene from a Rhizomucor species, the gene for the alpha-factor from *Saccharomyces cerevisiae*, an amylase or a protease gene from a Bacillus species, or the calf prepro-chymosin gene. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from Bacillus NCIB 11837, the Bacillus stearothermophilus alpha-amylase gene, the Bacillus licheniformis subtilisin gene, the Bacillus licheniformis beta-lactamase gene, the Bacillus stearothermophilus neutral proteases genes (nprT, nprS, nprM), or the Bacillus subtilis PrsA gene. Further signal peptides are described by Simonen and Palva, 1993, Microbiological Reviews 57: 109–137.

An effective signal peptide coding region for filamentous fungal host cells is the signal peptide coding region obtained from the Aspergillus oryzae TAKA amylase gene, Aspergillus niger neutral amylase gene, Rhizomucor miehei aspartic proteinase gene, Humicola lanuginosa cellulose gene, or Humicola lanuginosa lipase gene.

Useful signal peptides for yeast host cells are obtained from the genes for Saccharomyces cerevisiae alpha-factor and Saccharomyces cerevisiae inverse. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the Bacillus subtilis alkaline protease gene (aprE), the Bacillus subtilis neutral protease gene (nprT), the Saccharomyces cerevisiae alpha-factor gene, the Rhizomucor miehei aspartic proteinase gene, or the Myceliophthora thermophila laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

The nucleic acid constructs of the present invention may also comprise one or more nucleic acid sequences which encode one or more factors that are advantageous for directing the expression of the polypeptide, e.g., a transcriptional activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

A transcriptional activator is a protein which activates transcription of a nucleic acid sequence encoding a polypeptide (Kudla et al., 1990, EMBO Journal 9: 1355–1364; Jarai and Buxton, 1994, Current Genetics 26: 2238–244; Verdier, 1990, Yeast 6: 271–297). The nucleic acid sequence encoding an activator may be obtained from the genes encoding Bacillus stearothermophilus NprA (nprA), Saccharomyces cerevisiae heme activator protein 1 (hap1), Saccharomyces cerevisiae galactose metabolizing protein 4 (gal4), Aspergillus nidulans ammonia regulation protein (areA), and Aspergillus oryzae alpha-amylase activator (amyR). For further examples, see Verdier, 1990, supra and MacKenzie et al., 1993, Journal of General Microbiology 139: 2295–2307.

A chaperone is a protein which assists another polypeptide in folding properly (Hartl et al., 1994, TIBS 19: 20–25; Bergeron et al., 1994, TIBS 19: 124–128; Demolder et al., 1994, Journal of Biotechnology 32: 179–189; Craig, 1993, Science 260: 1902–1903; Gething and Sambrook, 1992, Nature 355: 33–45; Puig and Gilbert, 1994, Journal of Biological Chemistry 269: 7764–7771; Wang and Tsou, 1993, The FASEB Journal 7: 1515–11157; Robinson et al., 1994, Bio/Technology 1: 381–384; Jacobs et al., 1993, Molecular Microbiology 8: 957–966), The nucleic acid sequence encoding a chaperone may be obtained from the genes encoding Bacillus subtilis GroE proteins, Bacillus subtilis PrsA, Aspergillus oryzae protein disulphide isomerase, Saccharomyces cerevisiae calnexin, Saccharomyces cerevisiae BiP/GRP78, and Saccharomyces cerevisiae Hsp70. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, Yeast 10: 67–79; Fuller et al., 1989, Proceedings of the National Academy of Sciences USA 86: 1434–1438; Julius et al., 1984, Cell 37: 1075–1089; Julius et al., 1983, Cell 32: 839–852; U.S. Pat. No. 5,702, 934). The nucleic acid sequence encoding a processing protease may be obtained from the genes encoding Saccharomyces cerevisiae dipeptidylaminopeptidase, Saccharomyces cerevisiae Kex2, Yarrowia lipolytica dibasic processing endoprotease (xpr6), and Fusarium oxysporum metalloprotease (p45 gene).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, Aspergillus niger glucoamylase promoter, and the Aspergillus oryzae glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for mammalian cells are the dihydrofolate reductase (dfhr), hygromycin phosphotransferase (hygB), aminoglycoside phosphotransferase II, and phleomycin resistance genes. Suitable markers for yeast host cells are ADE2, HIS3, LEU2, LYS2, MET3, TRPl, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niad (nitrate reductase), pyrG (orotidine-5'-phosphate decarboxylase), sC (sulfate adenyltransferase), trpC (anthranilate synthase), as well as equivalents from other species. Preferred for use in an Aspergillus cell are the amdS and pyrG genes of *Aspergillus nidulans* or *Aspergillus oryzae* and the bar gene of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by culturing the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

A vector comprising a nucleic acid sequence of the present invention is introduced into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus,* or *Bacillus subtilis* cell. The introduction of a vector into a bacterial host cell may, for instance, be effected by protoplast transformation (see, e.g., Chang and Cohen, 1979, *Molecular General Genetics* 168: 111–115), by using competent cells (see, e.g., Young and Spizizin, 1961, *Journal of Bacteriology* 81: 823–829, or Dubnau and Davidoff-Abelson, 1971, *Journal of Molecular Biology* 56: 209–221), by electroporation (see, e.g., Shigekawa and Dower, 1988, *Biotechniques* 6: 742–751), or by conjugation (see, e.g., Koehler and Thorne, 1987, *Journal of Bacteriology* 169: 5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed below. Examples of Basidiomycota include mushrooms, rusts, and smuts. Representative groups of Chytridiomycota include, e.g., Allomyces, Blastocliella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Kluyveromyces, Pichia, and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sporobolomyces and Bullera) and Cryptococcaceae (e.g., genus Candida). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast,* Bacil, M., Horecker, B. J., and Stopani, A. O. M., editors, 2nd edition, 1987; *The Yeasts,* Rose, A. H., and Harrison, J. S., editors, 2nd edition, 1987; and *The Molecular Biology of the Yeast Saccharomyces,* Strathern et al., editors, 1981).

In an even more preferred embodiment, the yeast host cell is a cell of a species of Candida, Hansenula, Kluyveromyces, Pichia, Saccharomyces, Schizosaccharomyces, or Yarrowia.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell.

In a most preferred embodiment, the filamentous fungal host cell is an *Aspergillus awamori, Aspergillus foetidus, Aspergillus japonicus, Aspergillus nidulans, Aspergillus niger,* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, fusarium torulosum, Fusarium trichothecioides,* or *Fusarium venenatum* cell. In an even most preferred embodiment, the filamentous fungal parent cell is a *Fusarium venenatum* Nirenberg sp. nov.) cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma Iongibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. A suitable method of transforming Fusarium species is described by Malardier et al., 1989, *Gene* 78: 147–156 or in WO 96100787. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920. Mammalian cells may be transformed by direct uptake using the calcium phosphate precipitation method of Graham and Van der Eb (1978, *Virology* 52: 546).

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Aspergillus.

The present invention also relates to methods for producing a polypeptide of the present invention comprising (a) cultivating a host cell under conditions conducive for production of the polypeptide; and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670. Gene activation technology is based on activating a gene which is normally unexpressed in a cell or increasing expression of a gene which is expressed at very low levels in a cell. Gene activation technology includes methods of inserting an exogenous DNA construct containing a regulatory sequence, an exon, and/or a splice donor site into the genomic DNA of a cell in such a manner that the insertion results in the production of a new transcription unit in which the regulatory sequence, the exon, and/or the splice donor site are operably linked to and activate expression of the endogenous gene.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi*, Academic Press, CA, 1991). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining aminopeptidase activity are known in the art and include, e.g., measuring the initial rate of hydrolysis of a p-nitroanilide at 405 nm.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), SDS-PAGE, or extraction (see, e.g., *Protein Purification*, J.-C. Janson and Lars Ryden, editors, VCH Publishers, New York, 1989).

Removal or Reduction of Aminopeptidase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell.

The construction of strains which have reduced aminopeptidase activity may be conveniently accomplished by modification or inactivation of a nucleic acid sequence necessary for expression of the polypeptide having aminopeptidase activity in the cell. The nucleic acid sequence to be modified or inactivated may be, for example, a nucleic acid sequence encoding the polypeptide or a part thereof essential for exhibiting aminopeptidase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification include, but are not limited to, a leader, a polyadenylation sequence, a propeptide sequence, a signal sequence, and a termination terminator.

Modification or inactivation of the nucleic acid sequence may be performed by subjecting the cell to mutagenesis and selecting for cells in which the aminopeptidase producing capability has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced or no expression of aminopeptidase activity.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to inactivate or reduce production by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence encoding a polypeptide of the present invention may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) culturing the mutant cell under conditions conducive for production of the polypeptide; and (b) recovering the polypeptide. In the present context, the term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a still further aspect, the present invention relates to a method for producing a protein product essentially free of aminopeptidase activity by fermentation of a cell which produces both a polypeptide of the present invention as well as the protein product of interest. The method comprises adding an effective amount of an agent capable of inhibiting aminopeptidase activity to the fermentation broth either during or after the fermentation has been completed, recovering the product of interest from the fermentation broth, and optionally subjecting the recovered product to further purification.

In a still further alternative aspect, the present invention relates to a method for producing a protein product essentially free of aminopeptidase activity, wherein the protein product of interest is encoded by a DNA sequence present in a cell encoding a polypeptide of the present invention. The method comprises cultivating the cell under conditions permitting the expression of the product, subjecting the resultant culture broth to a combined pH and temperature treatment so as to reduce the aminopeptidase activity substantially, and recovering the product from the culture broth. Alternatively, the combined pH and temperature treatment may be performed on an enzyme preparation recovered from the culture broth. The combined pH and temperature treatment may optionally be used in combination with a treatment with an aninopeptidase inhibitor.

The combined pH and temperature treatment is preferably carried out at a pH in the range of 9–11 and a temperature in the range of 40–70° C. for a sufficient period of time to attain the desired effect, where typically, 30 to 60 minutes is sufficient.

In accordance with this aspect of the invention, it is possible to remove at least 60%, preferably at least 75%, more preferably at least 85%, still more preferably at least 95%, and most preferably at least 99% of the aminopeptidase activity. It is contemplated that a complete removal of aminopeptidase activity may be obtained by use of these methods.

The methods used for cultivation and purification of the product of interest may be performed by methods known in the art.

The methods of the present invention for producing an essentially aminopeptidase-free product is of particular interest in the production of eukaryotic polypeptides, in particular fungal proteins such as enzymes. The enzyme may be selected from, e.g., an amylolytic enzyme, a lipolytic enzyme, a proteolytic enzyme, a cellulytic enzyme, an oxidoreductase or a plant cell-wall degrading enzyme. Examples of such enzymes include an aminopeptidase, an amylase, an amyloglucosidase, a carbohydrase, a carboxypeptidase, a catalase, a cellulose, a chitinase, a cutinase, a cyclodextrin glycosyltransferase, a deoxyribonuclease, an esterase, a galactosidase, a beta-galactosidase, a glucoamylase, a glucose oxidase, a glucosidase, a haloperoxidase, a hemicellulase, an inverse, an isomerase, a laccase, a ligase, a lipase, a lyase, a mannosidase, an oxidase, a pectinolytic enzyme, a peroxidase, a phytase, a phenoloxidase, a polyphenoloxidase, a proteolytic enzyme, a ribonuclease, a transferase, a transglutaminase, or a xylanase. The aminopeptidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from aminopeptidase activity which is produced by a method of the present invention.

Methods of Producing Protein Hydrolysates

The polypeptides of the present invention may be used in the production of protein hydrolysates for enhancing the degree of hydrolysis and flavor development.

The present invention further relates to methods for using a polypeptide of the present invention in combination with an endopeptidase to produce a high degree of hydrolysis of a protein-rich material. The method comprises treating of a proteinaceous substrate with the polypeptide and an endopeptidase. The substrate may be treated with the enzymes concurrently or consecutively.

A polypeptide of the present invention is added to the proteinaceous substrate in an effective amount conventionally employed in protein hydrolysis processes, preferably in the range of from about 0.1 to about 100,000 aminopeptidase units per 100 g of protein, and more preferably in the range of from about 1 to about 10,000 aminopeptidase units per 100 g of protein. As defined herein, one aminopeptidase unit (APU) is the amount of enzyme needed to release 1 micromole of p-nitroanilide per minute from Leu-nitroanilide (Sigma Chemical Co., St. Louis, Mo.) under the specified conditions. Alternatively, the aminopeptidase may be employed preferably in the range of from about 0.5 to about 500 LAPU/g of protein, and more preferably in the range of from about 5 to about 50 LAPU/g of protein. LAPU is defined as the leucine aminopeptidase activity which is determined as described in AF 298/1-GB (available on request from Novo Nordisk A/S, Denmark).

The endopeptidase may be obtained from a strain of Bacillus, preferably *Bacillus licheniformis* or *Bacillus subtilis*, a strain of Staphylococcus, preferably *Staphylococcus aureus*, a strain of Streptomyces, preferably *Streptomyces thermovularis* or *Streptomyces griseus*, a strain of Actinomyces species, a strain of Aspergillus, preferably *Aspergillus aculeatus, Aspergillus awamori, Aspergillus foetidus, Aspergillus nidulans, Aspergillus niger,* or *Aspergillus oryzae*, or a strain of Fusarium, preferably *Fusarium venenatum*.

The endopeptidase is added to the proteinaceous substrate in an effective amount conventionally employed in protein hydrolysis processes, preferably in the range of from about 0.05 to about 15 AU/100 g of protein, and more preferably from about 0.1 to about 8 AU/100 g of protein. One AU (Anson Unit) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milli-equivalent of tyrosine. The analytical method AF 4/5 is available upon request from Novo Nordisk A/S, Denmark, which is incorporated herein by reference.

The enzymatic treatment, i.e., the incubation of the substrate with the enzyme preparations, may take place at any convenient temperature at which the enzyme preparation does not become inactivated, preferably in the range of from about 20° C. to about 70° C. In accordance with established practice, the enzyme preparations may be suitably inactivated by increasing the temperature of the incubation mixture to a temperature where the enzymes become inactivated, e.g., to above about 70° C., or similarly by decreasing the pH of the incubation mixture to a point where the enzymes become inactivated, e.g., below about 4.0.

Furthermore, the methods of the present invention result in enhancement of the degree of hydrolysis of a proteinaceous substrate. As used herein, the degree of hydrolysis (DH) is the percentage of the total number of amino bonds in a protein that has been hydrolyzed by a proteolytic enzyme. In a preferred embodiment, the protein hydrolysates have an increased content of Leu, Gly, Glu, Ser, Asp, Asn, Pro, Cys, Ala, and/or Gln, e.g., at least 1.1 times greater. In a more preferred embodiment, the protein hydrolysates have an increased content of Leu. In another more preferred embodiment, the protein hydrolysates have an increased content of Gly. In another more preferred embodiment, the protein hydrolysates have an increased content of Glu. In another more preferred embodiment, the protein hydrolysates have an increased content of Ser. In another more preferred embodiment, the protein hydrolysates have an increased content of Asp. In another more preferred embodiment, the protein hydrolysates have an increased content of Asn. In another more preferred embodiment, the protein hydrolysates have an increased content of Pro. In another more preferred embodiment, the protein hydrolysates have an increased content of Cys. In another more preferred embodiment, the protein hydrolysates have an increased content of Ala. In another more preferred embodiment, the protein hydrolysates have an increased content of Gln.

The present invention also relates to methods for obtaining a protein hydrolysate enriched in free glutamic acid and/or peptide bound glutamic acid residues, which method comprises:

(a) subjecting the substrate to a deamidation process; and
(b) subjecting the substrate to the action of a polypeptide having aninopeptidase activity.

The two steps may be performed simultaneously, or the second step may be performed subsequent to the first step.

These methods of the present invention produce protein hydrolysates of excellent flavor because glutamic acid (Glu), whether free or peptide bound, plays an important role in the flavor and palatability of protein hydrolysates. These method also produce protein hydrolysates having improved functionality, in particular, improved solubility, improved emulsifying properties, increased degree of hydrolysis, and improved foaming properties.

The conversion of amides (glutamine or asparagine) into charged acids (glutamic acid or) aspartic acid) via the liberation of ammonia is known as deamidation. Deamidation may take place as a non-enzymatic or as an enzymatic deamidation process.

In a preferred embodiment, the deamidation is carried out as an enzymatic deamidation process, e.g., by subjecting the substrate to a transglutaminase and/or peptidoglutaminase.

The transglutaminase may be of any convenient source including mammals, see e.g., JP 1050382 and JP 5023182, including activated Factor XIII, see e.g., WO 93/15234; those derived from fish, see e.g., EP 555,649; and those obtained from microorganisms, see e.g., EP 379,606, WO 96/06931 and WO 96/22366. In a preferred embodiment, the transglutaminase is obtained from an Oomycete, including a strain of Phytophthora, preferably *Phytophthora cactorum*, or a strain of Pythium, preferably *Pythium irregulare*, Pythium sp., *Pythium intermedium*, *Pythium ultimum*, or *Pythium periilum* (or *Pythium periplocum*). In another preferred embodiment, the transglutaminase is of bacterial origin and is obtained from a strain of Bacillus, preferably *Bacillus subtilis*, a strain of Streptoverticillium, preferably *Streptoverticillium mobaraensis*, *Streptoverticillium griseocarneum*, or *Streptoverticillium cinnamoneum*, and a strain of Streptomyces, preferably *Streptomyces lydicus*.

The peptidoglutaminase may be a peptidoglutaminase I (peptidyl-glutaminase; EC 3.5.1.43), or a peptidoglutaminase II (protein-glutamine glutaminase; EC 3.5.1.44), or any mixture thereof. The peptidoglutaminase may be obtained from a strain of Aspergillus, preferably *Aspergillus japonicus*, a strain of Bacillus, preferably *Bacillus circulans*, a strain of Cryptococcus, preferably *Cryptococcus albidus*, or a strain of Debaryomyces, preferably *Debaryomyces kloecheri*.

The transglutaminase is added to the proteinaceous substrate in an effective amount conventionally employed in deamidation processes, preferably in the range of from about 0.01 to about 5% (w/w), and more preferably in the range of from about 0.1 to about 1% (w/w) of enzyme preparation relating to the amount of substrate.

The peptidoglutaminase is added to the proteinaceous substrate in an effective amount conventionally employed in deamidation processes, preferably in the range of from about 0.01 to about 100,000 PGase Units per 100 g of substrate, and more preferably in the range of from about 0.1 to about 10,000 PGase Units per 100 g of substrate.

The peptidoglutaminase activity may be determined according to the procedure of Cedrangoro et al. (1965, *Enzymologia* 29: 143). According to this procedure, 0.5 ml of an enzyme sample, adjusted to pH 6.5 with 1 N NaOH, is charged into a small vessel. Then 1 ml of a borate pH 10.8 buffer solution is added to the vessel. The discharged ammonia is absorbed by 5 N sulphuric acid, and by use of Nessler's reagent the mixture is allowed to form color which is measured at 420 nm. One PGase unit is the amount of enzyme capable of producing 1 micromole of ammonia per minute under these conditions.

Alternatively, the peptidoglutaminase activity may be determined according to the procedure described in U.S. Pat. No. 3,857,967 or Example 20 below.

In step (b) of the methods of the present invention, the substrate is subjected to a polypeptide of the present invention. A polypeptide of the present invention is added to the proteinaceous substrate in an effective amount conventionally employed in protein hydrolysis processes, preferably in the range of from about 0.001 to about 0.5 AU/100 g of substrate, more preferably in the range of from about 0.01 to about 0.1 AU/100 g of substrate.

In another embodiment, the methods of the present invention for producing a hydrolysate enriched in free glutamic acid and/or peptide bound glutamic acid residues further comprise:

(c) subjecting the substrate to one or more unspecific acting endo- and/or exo-peptidase enzymes.

This step may take place simultaneously with steps (a) and (b), or may follow steps (a) and (b).

In a preferred embodiment, the unspecific acting endo- and/or exo-peptidase enzyme is obtained from a strain of Aspergillus, preferably *Aspergillus niger, Aspergillus oryzae,* or *Aspergillus sojae,* or a strain of Bacillus, preferably *Bacillus amyloliquefaciens, Bacillus lentus, Bacillus licheniformis,* or *Bacillus subtilis.*

The unspecific acting endo- and/or exo-peptidase enzyme is added to the substrate in an effective amount conventionally employed in protein hydrolysis processes, preferably in the range of from about 0.05 to about 15 CPU/100 g of substrate, and more preferably in the range of from about 0.1 to about 5 CPU/100 g of substrate. One CPU (Casein Protease Unit) is defined as the amount of enzyme liberating 1 micromole of primary amino groups (determined by comparison with a serine standard) per minute from casein under standard conditions, i.e., incubation for 30 minutes at 25° C. and pH 9.5. The analytical method AF 228/1, which is incorporated herein by reference, is available upon request from Novo Nordisk A/S, Bagsvaerd, Denmark.

Each enzymatic treatment may take place at any temperature at which the enzyme preparation does not become inactivated, preferably in the range of from about 20° C. to about 70° C. The enzyme preparation may then be inactivated by increasing the temperature, e.g., to above about 70° C., or by decreasing the pH, e.g., below about 4.0.

The proteinaceous substrate used in the methods of the present invention may consist of intact proteins, prehydrolyzed proteins (i.e., peptides), or a mixture thereof. The proteinaceous substrate may be of vegetable or animal origin. Preferably, the proteinaceous substrate is of vegetable origin, e.g., soy protein, grain protein, e.g., wheat gluten, corn gluten, barley, rye, oat, rice, zein, lupine, cotton seed protein, rape seed protein, peanut, alfalfa protein, pea protein, fabaceous bean protein, sesame seed protein, or sunflower. A proteinaceous substrate of animal origin may be whey protein, casein, meat proteins, fish protein, red blood cells, egg white, gelatin, or lactoalbumin.

The present invention also relates to protein hydrolysates produced by these methods.

Other Uses

The present invention also relates to methods of deactivating enzymes with a polypeptide of the present invention.

Furthermore, a polypeptide of the present invention may be useful for a number of purposes in which a specific cleavage of peptide sequences is desirable. For instance, some proteins or peptides are synthesized in the form of inactive precursors comprising a number of additional amino acid residues at the N-terminal of the mature protein. A polypeptide of the present invention could provide the necessary post-translational processing to activate such precursor proteins.

Compositions

In a still further aspect, the present invention relates to polypeptide compositions comprising a polypeptide of the present invention. Preferably, the compositions are enriched in a polypeptide of the present invention. In the present context, the term "enriched" indicates that the aminopeptidase activity of the polypeptide composition has been increased, e.g., with an enrichment factor of 1.1.

The polypeptide composition may comprise a polypeptide of the invention as the major enzymatic component, e.g., a mono-component polypeptide composition. Alternatively, the composition may comprise multiple enzymatic activities, such as an aminopeptidase, an amylase, a carbohydrase, a carboxypeptidase, a catalase, a cellulose, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an inverse, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, or a xylanase. The additional enzyme(s) may be producible by means of a microorganism belonging to the genus Aspergillus, preferably *Aspergillus aculeatus, Aspergillus awamori, Aspergillus niger,* or *Aspergillus oryzae,* or Trichoderma, Humicola, preferably *Humicola insolens,* or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum.*

In a preferred embodiment, the invention relates to a flavor-improving composition comprising a polypeptide with aminopeptidase activity and a suitable carrier. Any suitable carrier known in the art may be used. In another preferred embodiment, the flavor-improving composition further comprises an endopeptidase. In another preferred embodiment, the flavoring composition further comprises one or more unspecific-acting endo- and/or exo-peptidase enzymes. In another preferred embodiment, the flavoring composition further comprises one or more specific-acting endo- and/or exo-peptidase enzymes.

In a preferred embodiment, the specific acting proteolytic enzyme is an endopeptidase such as a glutamyl endopeptidase (EC 3.4.21.19); a lysyl endopeptidase (EC 3.4.21.50); a leucyl endopeptidase (EC 3.4.21.57); a glycyl endopeptidase (EC 3.4.22.25); a prolyl endopeptidase (EC 3.4.21.26); trypsin (EC 3.4.21.4) or a trypsin-like (lysine/arginine specific) endopeptidase; or a peptidyl-Asp metalloendopeptidase (EC 3.4.24.33).

The glutamyl endopeptidase (EC 3.4.21.19) may preferably be obtained from a Bacillus strain, in particular *Bacillus licheniformis* and *Bacillus subtilis,* a Staphylococcus strain, in particular *Staphylococcus aureus,* a Streptomyces strain, in particular *Streptomyces thermovulgaris* and *Streptomyces griseus,* or a Actinomyces strain.

The lysyl endopeptidase (EC 3.4.21.50) may preferably be obtained from a Achromobacter strain, in particular *Achromobacter lyticus,* a Lysobacter strain, in particular *Lysobacter enzymogenes,* or a Pseudomonas strain. in particular *Pseudomonas aeruginosa.*

The leucyl endopeptidase (EC 3.4.21.57) may be of plant origin.

The glycyl endopeptidase (EC 3.4.22.25) may preferably be obtained from the papaya plant (*Carica papaya*).

The prolyl endopeptidase (EC 3.4.21.26) may preferably be obtained from a Flavobacterium strain, or it may be of plant origin.

The trypsin-like endopeptidase may preferably be obtained from a Fusarium strain, in particular *Fusarium oxysporum,* e.g., as described in WO 89/06270 or WO 94/25583.

The peptidyl-Asp metalloendopeptidase (EC 3.4.24.33) may preferably be obtained from a Pseudomonas strain, in particular *Pseudomonas fragi.*

In another preferred embodiment, the specific acting proteolytic enzyme is an exo-peptidase that may act from either end of the peptide.

In a preferred embodiment, the specific acting proteolytic enzyme is an aminopeptidase such as a leucyl aminopeptidase (EC 3.4.11.1); or a tripeptide aminopeptidase (EC 3.4.11.4).

In another preferred embodiment, the specific acting proteolytic enzyme is a carboxypeptidase such as a proline carboxypeptidase (EC 3.4.16.2); a carboxypeptidase A (EC 3.4.17.1); a carboxypeptidase B (EC 3.4.17.2); a carboxypeptidase C (EC 3.4.16.5); a carboxypeptidase D (EC 3.4.16.6); a lysine (arginine) carboxypeptidase (EC 3.4.17.3); a glycine carboxypeptidase (EC 3.4.17.4); an alanine carboxypeptidase (EC 3.4.17.6); a glutamate carboxypeptidase (EC 3.4.17.11); a peptidyl-dipeptidase A (EC 3.4.15.1); or a peptidyl-dipeptidase (EC 3.4.15.5).

The polypeptide compositions may be prepared in accordance with methods known in the art and may be in the form of a liquid or a dry composition. The polypeptide may be stabilized by methods known in the art.

The present invention also relates to food products, e.g., baked products, comprising a protein hydrolysate obtained by the methods of the present invention. Such food products exhibit enhanced organoleptic qualities, such as improvement in flavor, palatability, mouth feel, aroma and crust color.

In the present context, the term "baked products" includes any food prepared from dough, either of a soft or a crisp character. Examples of baked products, whether of a white, light or dark type, which may be advantageously produced by the present invention, are bread, in particular white, whole-meal or rye bread, typically in the form of loaves or rolls; French baguette-type breads; pita breads; tacos; cakes; pancakes; biscuits; crisp breads; and the like.

Such baked products are conventionally prepared from a dough which comprises flour and water, and which is typically leavened. The dough may be leavened in various ways, such as by adding sodium bicarbonate or the like, or by adding a leaven (fermenting dough), but the dough is preferably leavened by adding a suitable yeast culture such as a culture of Saccharomyces cerevisiae (baker's yeast). Any of the commercially available Saccharomyces cerevisiae strains may be employed.

Further, the dough used in the preparation of the baked products may be fresh or frozen. The preparation of frozen dough is described by K. Kulp and K. Lorenz in "Frozen and Refrigerated Doughs and Batters". A flavor improving composition of the present invention is typically included in the dough in an amount in the range of 0.01–5%, more preferably 0.1–3%.

In the methods of the present invention, a polypeptide of the present invention, an endopeptidase, a transglutaminase, a peptidoglutaminase, one or more specific and/or unspecific acting endo- and/or exo-peptidase enzymes, and/or one or more enzymes specified above may be added, either separately or concurrently, to the mixture from which the dough is made or to any ingredient, e.g., flour, from which the dough is to be made.

The present invention further relates to a pre-mix, e.g., in the form of a flour composition, for dough and/or baked products made from dough, wherein the pre-mix comprises a polypeptide or a flavor-improving composition of the invention and a carrier or baking ingredient, and optionally one or more other enzymes specified above.

In another embodiment, the pre-mix comprises a hydrolysate obtained by the methods of the invention.

The pre-mix may be prepared by mixing the relevant enzymes with a suitable carrier such as flour, starch, a sugar or a salt. The pre-mix may contain other dough-improving and/or bread-improving additives.

In the present context, the term "pre-mix" is a mixture of baking agents, normally including flour, which has been prepared to permit storage under designated conditions and provide convenience in handling during dough preparation processes. Such a pre-mix may be of advantageous use in industrial and commercial bread-baking plants and facilities, as well as in retail bakeries.

The present invention also relates to the use of a hydrolysate produced by the methods of the invention as an additive to food products, such as baked foods, to enhance organoleptic qualities, such as flavor, palatability and aroma.

The hydrolysates enriched in free glutamic acid and/or peptide bound glutamic acid residues obtained by the methods of the present invention may be used in various industrial applications, in particular, where there is a need for the incorporation of functional proteins.

For example, the present invention also relates to food products comprising a hydrolysate enriched in free glutamic acid and/or peptide bound glutamic acid residues obtained by the method of the invention and to animal feed additives comprising a hydrolysate enriched in free glutamic acid and/or peptide bound glutamic acid residues obtained by the methods of the present invention.

The present invention is further described by the following examples which should not be construed as limiting the scope of the invention.

EXAMPLES

Example 1

Purification of FLAVOURZYME™ Aminopeptidase II

Aminopeptidase was purified from a FLAVOURZYME™ broth (Novo Nordisk A/S, Bagsvaerd, Denmark). The FLAVOURZYME™ broth was produced by cultivation of Aspergillus oryzae strain 1568 (ATCC 20386) in a medium composed of carbon and nitrogen sources and trace metals. First, the broth (20 ml containing 720 mg of protein) was diluted with 180 ml of 20 mM sodium phosphate pH 7.0 buffer and filtered using Nalgene Filterware equipped with a 0.45 µm filter (Nalgene, Rochester, N.Y.). The filtered solution was loaded onto a 24×130 mm column containing 31 ml of Q-Sepharose, Big Beads (Pharmacia Biotech AB, Uppsala, Sweden) pre-equilibrated with 20 mM sodium phosphate pH 7.0 buffer. The protein was eluted using pH gradients from 7.0 (20 mM sodium phosphate buffer) to 5.0 (20 mM sodium acetate buffer), from 5.0 to 3.5 (20 mM sodium acetate buffer), and then from 3.5 to 3.0 (20 mM sodium acetate buffer). Fractions eluting between pH 3.5 and 3.0 were collected, pooled, and concentrated to 20 ml by ultrafiltration with a PM10 membrane (Amicon, New Bedford, Mass.).

The concentrated solution was diluted with 100 ml of 20 mM sodium phosphate pH 7.0 buffer and then loaded onto a 20×100 mm column containing Pharmacia MonoQ Beads (Pharmacia Biotech AB, Uppsala, Sweden) pre-equilibrated with 20 mM sodium phosphate pH 7.0 buffer. The protein was eluted with a 0 to 0.4 M NaCl gradient in 20 mM sodium phosphate pH 7.0 buffer. The fractions between 0.330 and 0.343 M NaCl were collected, pooled, and concentrated using ultrafiltration against 20 mM sodium acetate pH 4.0 buffer.

The purified preparation was found to contain three major bands judged by SDS-PAGE analysis. The sample consisted of components with molecular weights of approximately 65, 50 and 33 kDa.

Example 2

Amino Acid Sequencing of Aminopeptidase II

An aliquot of the purified aminopeptidase II preparation described in Example 1 was electrophoresed and subsequently blot-transferred to a PVDF membrane (Novex, San Diego, Calif.) using 10 mM CAPS (3-[cyclohexylamino]-1-propanesulfonic acid) pH 11 in 10% methanol for 2 hours. The PVDF membrane was stained with 0.1% Coommassie Blue R-250 in 40% methanol/1% acetic acid for 20 seconds and destained in 50% ethanol to observe the protein bands. Three components at 65, 50, and 33 kDa were excised and subjected to amino terminal sequencing on an Applied Biosystems Model 476A protein sequencer (Applied Biosystems, Inc., Foster City, Calif.) using a blot cartridge and liquid phase TFA delivery according to the manufacturer's instructions. All three components yielded the same amino terminal sequence, RALVSPDEFPEDIQLEDLLEG-SQQLEDFAY (amino acids 17 to 47 of SEQ ID NO: 2.

A 300 μl sample of the protein was dried on a Savant Speed Vac AS160 (Savant Instruments, Farmingdale, N.Y.) and then reconstituted with 300 μl of 70% formic acid (aqueous). A few crystals of cyanogen bromide were added and incubated at room temperature in the dark overnight. The sample was redried in the Speed Vac and reconstituted in Tricine sample buffer (Novex, San Diego, Calif.). The cyanogen bromide cleavage fragments were separated using a 10–20% Tricine SDS-polyacrylamide gel into bands of 6, 10, 15, 22, 27, 40 and 50 kDa and blot-transferred to a PVDF membrane. The 6, 10, 15, and 22 kDa bands were excised and subjected to amino terminal sequencing.

The amino terminal sequences of the 15 and 22 kDa bands were identical to the amino terminal sequence above, while the sequences of the 6 and 10 kDa bands were both determined to contain the sequence TYSPSVEVTADVAVVKN-LGTSEADYPDVEGKVAL (amino acids 108 to 142 of SEQ ID NO: 2.

Example 3

Aspergillus oryzae Strain 1568 RNA Isolation

Aspergillus oryzae strain 1568 was cultivated in a fermentation tank in a medium composed of 7.5 g of potato starch, 10 g of soy bean meal, 2 g of $KH_2PO_4$, 5 g of $Na_2HPO_4$-$2H_2O$, and 0.1 g of $ZnSO_4$-$7H_2O$ per liter. A two liter sample was taken after five days of growth at 30° C., and the mycelia were collected, frozen in liquid $N_2$, and stored at −80° C. Total RNA was prepared from the frozen, powdered mycelia of Aspergillus oryzae 1568 by extraction with guanidinium thiocyanate followed by ultracentrifugation through a 5.7 M cesium chloride cushion (Chirgwin et al., 1979, Biochemistry 18: 5294–5299). Poly(A)+ RNA was isolated by oligo(dT)-cellulose affinity chromatography according to Aviv and Leder (1972, Proceedings of the National Academy of Sciences USA 69: 1408–1412).

Example 4

Construction of a cDNA Library

Double-stranded cDNA was synthesized from 5 μg of Aspergillus oryzae 1568 poly(A)+ RNA of Example 3 using the procedure described by Gubler and Hoffman (1983, Gene 25: 263–269) and Sambrook et al. (1989, Molecular Cloning: A Laboratory Manual, Cold Spring Harbor Press, Cold Spring Harbor, N.Y.), except that an oligo(dT)-NotI anchor primer, instead of an oligo(dT)12–18 primer, was used in the first strand reaction. After synthesis, the cDNA was treated with Mung bean nuclease (Life Technologies, Gaithersburg, Md.), blunt-ended with T4 DNA polymerase (Boehringer Mannheim, Indianapolis, Ind.), and ligated to non-palindromic BstXI adaptors (Invitrogen, San Diego, Calif.), using about 50-fold molar excess of the adaptors. The adapted cDNA was digested with NotI, size-fractionated for 1.2–3.0 kb cDNAs by agarose gel electrophoresis, and ligated into pYES2.0 (Invitrogen, San Diego, Calif.) cleaved with BstXI/NotI. The ligation mixture was transformed into electrocompetent E. coli DH10B cells (Life Technologies, Gaithersburg, Md.) according to the manufacturer's instructions. The library consisting of 1×10$^6$ independent clones was stored as individual pools (25,000–30,000 colony forming units/pool) in 20% glycerol at −80° C., and as double stranded cDNA and ligation mixture at −20° C.

Example 5

Genomic DNA Extraction

Aspergillus oryzae 1568 was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg per ml and the mixture was then incubated at 37° C. for 30 minutes. Proteinase K (200 μg/ml) was added and the tube was incubated an additional one hour at 37° C. Finally, the sample was extracted twice with phenol:chloroform:isoamyl alcohol and the DNA precipitated with ethanol. The precipitated DNA was washed with 70% ethanol, dried under vacuum, resuspended in TE buffer, and stored at 4° C.

Example 6

PCR Amplification of Aspergillus oryzae 1568 Aminopeptidase II

Based on the amino acid sequences of the Aspergillus oryzae 1568 aminopeptidase II partial peptides described in Example 2, the degenerate oligonucleotide primers shown below were synthesized with an Applied Biosystems Model 394 DNA/RNA Synthesizer, according to the manufacturer's instructions, to PCR amplify aminopeptidase II gene fragments from Aspergillus oryzae 1568 genomic DNA.

Forward primer: 5'-CCIGAYGARTTYCCIGA
   RGA-3' (SEQ ID NO:3)

Reverse primer: 5'-RTTYTTIACIACIGCIACRTCIGCIG-
   TIACYTCIAC-3' (SEQ ID NO:4)

(R=A or G, Y=C or T, N=G or A or C or T, H=A or C or T, I=Inosine)

Amplification reactions (50 μl) were prepared using approximately 1 μg of Aspergillus oryzae 1568 genomic DNA, prepared as described in Example 5, as the template. Each reaction contained the following components: 1 µg of genomic DNA, 40 pmol of the forward primer, 40 pmol of the reverse primer, 200 µM each of dATP, dCTP, dGTP, and dTTP, 1×Taq polymerase buffer (Perkin-Elmer Corp., Branchburg, N.J.), and 2.5 Units of Taq polymerase (Perkin-Elmer Corp., Branchburg, N.J.). The reactions were incubated in a Perkin-Elmer Model 480 Thermal Cycler programmed as follows; Cycle 1 at 94° C. for 5 minutes, 50° C. for 2 minutes, and 72° C. for 2 minutes; and Cycles 2–26 at 94° C. for 2 minutes, 50° C. for 1 minute, and 72° C. for 2 minutes. The reaction products were isolated on a 1.5% agarose gel (Eastman Kodak, Rochester, N.Y.) where a 309 bp product band was excised from the gel and purified using Qiaex II (Qiagen, Chatsworth, Calif.) according to the manufacturer's instructions. The purified PCR product was subsequently cloned into a pCRU vector (Invitrogen, San Diego, Calif.) and the DNA sequence was determined using lac forward and reverse primers (New England BioLabs, Beverly, Mass.).

The aminopeptidase II gene segment (309 bp) consisting of 103 codons was amplified from *Aspergillus oryzae* 1568 with the aminopeptidase II-specific PCR primers described above. DNA sequence analysis showed that the amplified gene segment encoded a portion of the corresponding *Aspergillus oryzae* 1568 aminopeptidase II gene. The aminopeptidase II gene segment was used to probe the *Aspergillus oryzae* 1568 cDNA library described in Example 5.

Example 7

Identification of *Aspergillus oryzae* 1568 Aminopeptidase II Clones

The *Aspergillus oryzae* 1568 cDNA library was plated on Luria plus 50 µgl/ml carbenicillin agar plates. Colony lifts (Maniatis et al., 1982, *Molecular Cloning, A Laboratory Manual,* Cold Spring Harbor Press, Cold Spring Harbor, N.Y.) were performed on approximately 10,000 colonies and the DNA was cross-linked onto membranes (Hybond N+, Amersham, Arlington Heights, Ill.) using a UV Stratalinker (Stratagene, La Jolla, Calif.). The membranes were soaked for three hours at 45° C. in a hybridization solution containing 5×SSPE, 0.3% SDS, 50% formamide, and 10 µg/ml of denatured and sheared herring sperm DNA. The aminopeptidase II gene fragment isolated from the *Aspergillus oryzae* 1568 as described in Example 6 was radiolabeled using the Random Primed DNA Labeling Kit (Boehringer Mannheim, Mannheim, Germany), denatured by adding NaOH to a final concentration of 0.1 M, and added to the hybridization solution at an activity of approximately $1\times10^6$ cpm per ml of hybridization solution. The mixture was incubated overnight at 45° C. in a shaking water bath. Following incubation, the membranes were washed three ties in 2×SSC with 0.2% SDS at 55° C. The membranes were then dried on blotting paper for 15 minutes, wrapped in SaranWrap™, and exposed to X-ray film for 48 hours at −70° C. with intensifying screens (Kodak, Rochester, N.Y.).

Eleven colonies, produced strong hybridization signals with the probe. The eleven colonies were inoculated into five ml of LB plus 50 µg/ml carbenicillin medium and grown overnight at 37° C. Miniprep DNA was prepared from each of these clones using the Wizard 373 DNA Purification Kit (Promega, Madison, Wis.). Clone 9 and clone 10 contained aminopeptidase II encoding sequence, as confirmed by DNA sequencing. Clone 9 (pEJG18) was full length. The plasmid pEJG18 was subcloned in *E. coli* DH5α cells to produce *E. coli* DH5α EJG18.

Example 8

DNA Sequence Analysis of *Aspergillus oryzae* 1568 Aminopeptidase II Gene

DNA sequencing of the aminopeptidase II gene contained in pEJG18 in *E. coli* DH5α EJG18 described in Example 7 was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virology Methods* 38: 47–60). Oligonucleotide sequencing primers were designed to complementary sequences in the aminopeptidase II gene and were synthesized on an Applied Biosystems Model 394 DNA/RNA Synthesizer according to the manufacturer's instructions.

The nucleotide sequence of the gene encoding the *Aspergillus oryzae* 1568 aminopeptidase II and the deduced amino acid sequence thereof is shown in FIG. 1 (SEQ ID NOS:1 and 2, respectively). Sequence analysis of the cloned insert revealed a large open reading frame of 1488 nucleotides (excluding the stop codon) encoding a protein of 496 amino acids sequence (SEQ ID NO:2). The G+C content of this open reading frame is 58%. Based on the rules of van Heijne (van Heijne, 1984, *Journal of Molecular Biology* 173: 243–251), the first 15 amino acids likely comprise a secretory signal peptide which directs the nascent polypeptide into the endoplasmic reticulum (double underlined in FIG. 1).

The amino acid sequences of the partial peptides derived from the purified aminopeptidase II as described in Example 2 are underlined in FIG. 1 and were consistent with those found in the deduced amino acid sequence (SEQ ID NO:2) of the *Aspergillus oryzae* 1568 aminopeptidase II cDNA.

Using the Clustal alignment program (Higgins, 1989, supra) to compare the deduced amino acid sequence of the *Aspergillus oryzae* 1568 aminopeptidase II to that of the *Saccharmyces cerevisiae* aminopeptidase II Y (SEQ ID NO:5), a 33.7% identity was observed.

Example 9

Construction of an *Aspergillus oryzae* 1568 Aminopeptidase II Expression Vector for an Aspergillus Host Two synthetic oligonucleotide primers shown below were designed to PCR amplify the *Aspergillus oryzae* A1568 aminopeptidase II gene coding sequence from plasmid pEJG 18 (*E. coli* DH5α-EJG 18) for subcloning and expression in an Aspergillus host.

Forward primer: 5'-ATGATGAGGTCGCTTTTGTG
    GGC-3'    (SEQ ID NO:6)

Reverse primer: 5'-GGGATGCATCTATGCCTCGA
    CTT-3    (SEQ rLD NO:7)

Bold letters represent coding sequence.

In order to facilitate the subcloning of the gene fragment into an expression vector designated pMWR3 (FIG. 2), a NsiI restriction enzyme site was introduced at the 3' end of the aminopeptidase II gene. The 5' end was left blunt with an addition of ATG for insertion into the SwaI site. The vector pMWR3 contained the TAKA promoter and terminator as regulatory sequences. Since the plasmid does not contain a selectable marker for fungal transformations, it was cotransformed with pToC90 (WO 91/17243) which contains amdS as the selectable marker.

Figure 3:
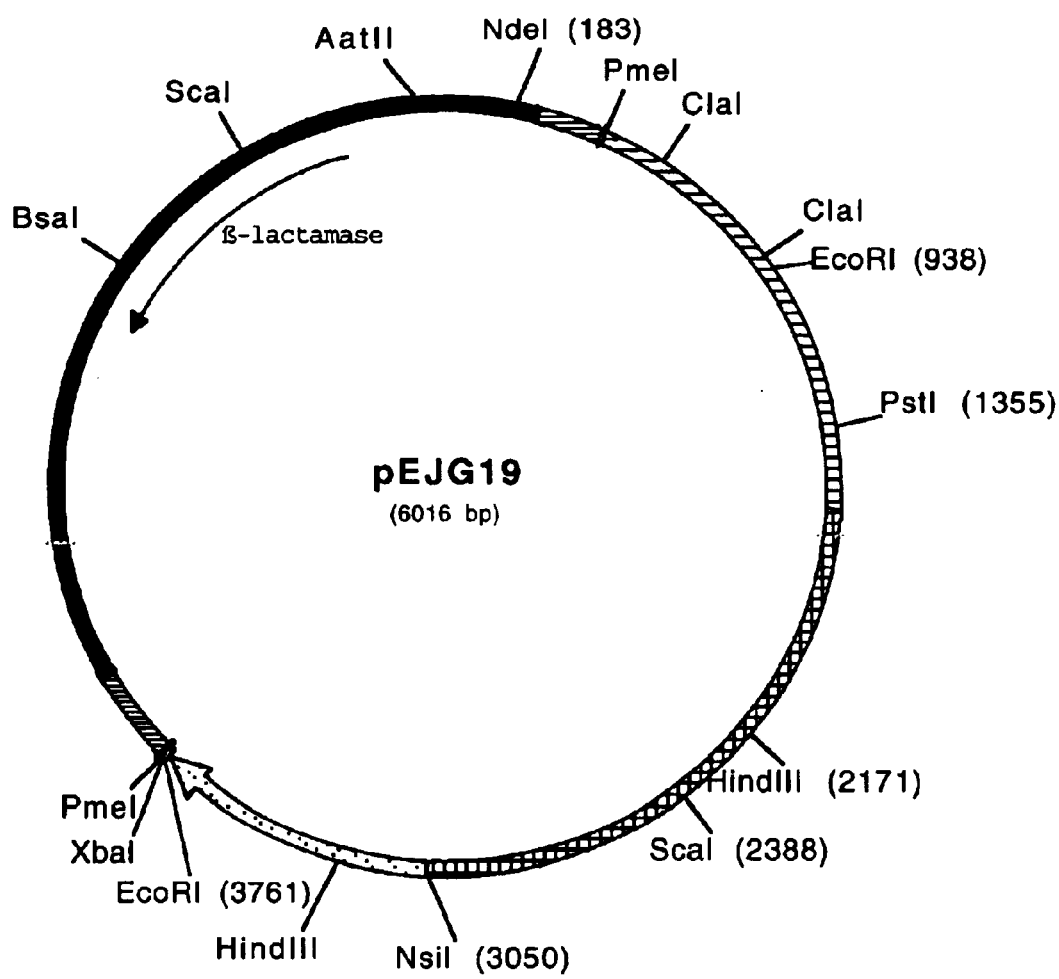
FIG. 3 shows a restriction map of pEJG19.

Fifty picomoles of each of the primers above were used in a PCR reaction (50 μl) containing 70 ng of pEJG18 (an *Aspergillus oryzae* 1568 cDNA clone in pYES2), 1×Pwo Buffer (Boehringer Mannheim, Indianapolis, Ind.), 8 μl of a 10 mM blend of DATP, dTTP, dGTP, and dCTP, and 2.5 units of PwoI (Boehringer Mannheim, Indianapolis, Ind.). The amplification conditions were one cycle at 94° C. for 2 minutes, 55° C. for 30 seconds, and 72° C. for 1 minute; 9 cycles at 94° C. for 15 seconds, 55° C. for 30 seconds, and 72° C. for 1 minutes; 15 cycles at 94° C. for 15 seconds, 55° C. for 30 seconds, and 72° C. for 1 minute, with an extension of 20 seconds per cycle; and a final cycle of 94° C. for 15 seconds, 55° C. for 30 seconds, and 72° C. for 7 minutes. The beat block then went to a 4° C. soak cycle. The amplified 1500 bp DNA fragment was purified by gel electrophoresis and Qiaex II. The aminopeptidase clone was digested with NsiI (using conditions specified by the manufacturer). The fragment was phenol-chloroform extracted and ethanol precipitated. The cut fragment was cloned into pMWR3 that had been previously cut with SwaI and NsiI resulting in the expression plasmid pEJG19 (FIG. 3) in which transcription of the aminopeptidase II gene was under the control of the TAKA promoter. The plasmid pEJG19 was transformed into *E. coli* DH5α cells (Life Technologies, Gaithersburg, Md.). An *E. coli* transformant containing the pEJG19 plasmid was isolated and plasmid DNA was prepared according to procedures described by Sambrook et al., 1989, supra.

Example 10

Expression of the *Aspergillus oryzae* 1568 Aminopeptidase II Gene in *Aspergillus oryzae*

Plasmid pEJG19 was introduced into an alkaline protease-deficient *Aspergillus oryzae* host JaL142-6 using the following protoplast transformation methods. The transformation was conducted with protoplasts at a concentration of ca. $2 \times 10^7$ protoplasts per ml. One hundred μl of protoplasts were placed on ice with ca. 5 μg of pEJG19 and 5 μg of pTOC90; 250 μl of 60% PEG 4000, 10 mM Tris-HCl, pH 7.5, 10 mM $CaCl_2$ was added, and the protoplasts were incubated at 37° C. for 30 minutes. Three mls of STC (1.2 M Sorbitol, 10 mM Tris-HCl, pH 7.5, and 10 mM $CaCl_2$) was added. The solution was mixed gently and poured onto COVE transformation plates (per liter: 0.52 g of KCl, 0.52 g of $MgSO_4$-$7H_2O$, 1.52 g of $KH_2PO_4$, 1 ml of trace metals described below, 342.3 g of sucrose, 25 g of Noble agar, 10 ml of 1 M acetamide, 10 ml of 3 M CsCl). The trace metals solution (1000×) was comprised of 22 g of $ZnSO_4$-$7H_2O$, 11 g of $H_3BO_3$, 5 g of $MnCl_2$-$4H_2O$, 5 g of $FeSO_4$-$7H_2O$, 1.6 g of $CoCl_2$-$5H_2O$, 1.6 g of $(NH_4)_6Mo_7O_{24}$, and 50 g of $Na_4EDTA$ per liter. Plates were incubated 7 days at 37° C. Transformants were transferred to plates of the same medium and incubated 2 days at 37° C. Totally, 140 transformants were recovered by their ability to grow on COVE medium using acetamide as sole nitrogen source.

The transformants were grown for 4 days at 34° C., 200 rpm in 24 well plates containing 1 ml per well of 25% MY50 medium diluted with 75% MY50 salts. MY50 was composed per liter of 50 g of maltodextrin, 2.0 g of $MgSO_4$-$7H2O$, 10 g of $KH_2PO_4$, 2 g of citric acid, 10 g of yeast extract, 2.0 g of urea, 2 g of $K_2SO_4$ and 0.5 ml of trace elements solution adjusted to pH 6.0. The trace metals solution was compsoed per liter of 14.3 g of $ZnSO_4$-$7H_2O$, 2.5 g of $CuSO_4$-$5H_2O$, 0.5g of $NiCl_2$-$6H_2O$, 13.8 g of $FeSO_4$-$7H_2O$, 8.5 g of $MnSO_4$-$H_2O$, 3 g of citric acid. The MY50 salts was compsoed per liter of 2.0 g of $MgSO_4$-$7H_2O$, 10 g of $KH_2PO_4$, 2 g of citric acid, and 2 g of $K_2SO_4$, pH 6.0.

Each of the 140 wells were assayed for aminopeptidase II activity using Leu-pNA (hydrochloride salt) as substrate. In a 96 well microtiter plate, 4 μl of supernatant was added to 100 μl of 1 mg/ml of Leu-pNA in 50 mM sodium phosphate pH 7.5 buffer. The absorbance at 405 nm was monitored.

Four transformants, 20, 88, 90, and 137, with the highest level of aminopeptidase II activity were then grown in 125 ml shake flasks for 4 days at 34° C. containing 25 ml of MY50 medium.

Samples were assayed on day 2, 3, and 4 for aminopeptidase II activity by mixing 100 μl of 10-fold diluted supernatant with 100 μl of 2 mg/ml Leu-pNA in 50 mM sodium phosphate pH 7.5 buffer. Transformants 20, 90, and 137 were the highest producers, for For purification of the aminopeptidase II, transformants 20 and/or 90 were grown in shake flasks as above or in a fermentation medium composed of suitable carbon and nitrogen sources.

Example 11

Purification of Recombinant *Aspergillus oryzae* 1568 Aminopeptidase II Produced in Aspergillus The combined supernatants from the shake flask broths described in Example 10 were combined (approximately 100 mg of protein in approximately 100 ml) and was diluted to 3.7 mS and adjusted to pH 7.0. The diluted sample was then loaded onto Q-Sepharose, Big Beads, pre-equilibrated with 20 mM sodium phosphate pH 7.0 buffer. The aminopeptidase II was eluted with a 0–0.4 M NaCl gradient in 20 mM sodium phosphate pH 7.0 buffer followed by a wash with 0.4 M NaCl. Fractions were assayed for aminopeptidase II activity by mixing 100 μl of each fraction with 100 μl of 2 mg of leu-pNA per ml of 50 mM sodium phosphate pH 7.5 buffer. The assay results indicated that the aminopeptidase II eluted at the end of the gradient and during the 0.4 M NaCl wash. Analysis by SDS-PAGE revealed that the enzyme was homogeneous.

Example 12

Construction of an *Aspergillus oryzae* 1568 Aminopeptidase II Expression Vector for a Fusarium Host Two synthetic oligonucleotide primers shown below were designed to PCR amplify the *Aspergillus oryzae* A 1568 aminopeptidase II gene coding sequence from plasmid pEJG 18 (*E. coli* DH5α-EJG18) for subcloning and expression in a Fusarium host.

Forward primer: 5'-AITTAAATcaccATGAG-
   GTCGCTTTTGTGGGC-3'   (SEQ ID NO:8)

Reverse primer: 5'-GGGTTAATTAACTATGCCTCGACT-
   TGAGAATG-3'   (SEQ ID NO:9)

Bold letters represent coding sequence. Small case represents a Kozak consensus sequence to enhance expression. (Kozak, 1981, *Nucleic Acids Research* 12. 857–872)

Figure 4:
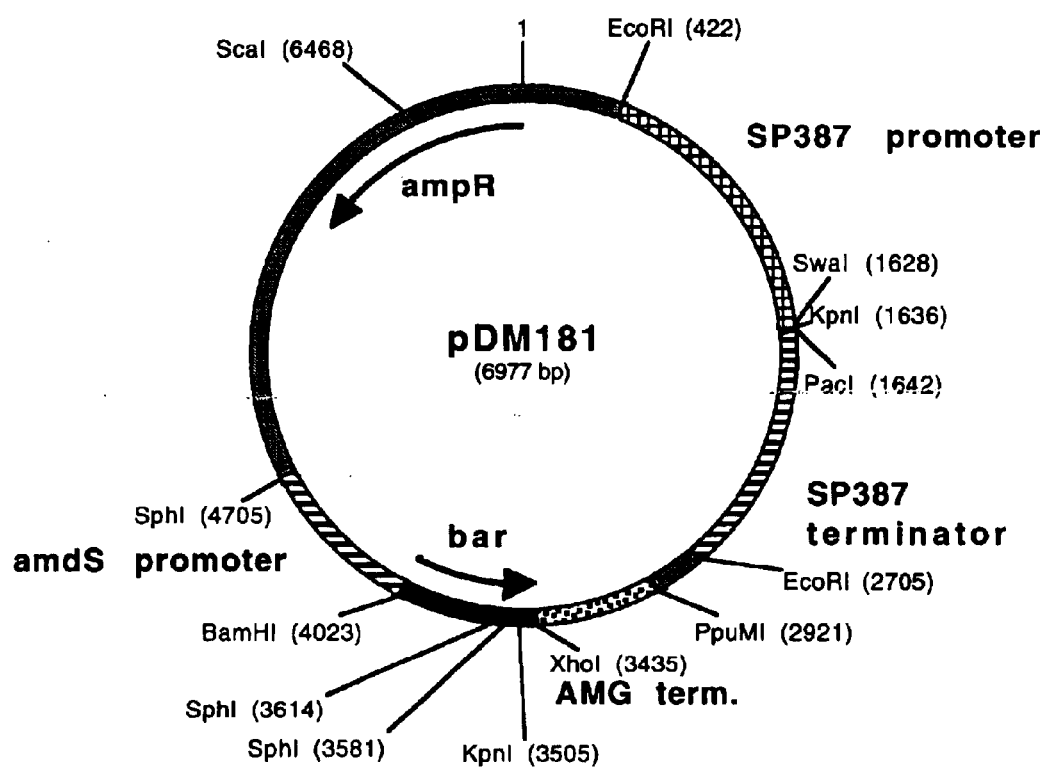
FIG. 4 shows a restriction map of pDM181.

In order to facilitate the subcloning of the gene fragment into an expression vector designated pDM 181 (FIG. 4), SwaI and PacI restriction enzyme sites were introduced at the 5' and 3' end of the aminopeptidase II gene, respectively. The vector pDM181 contained the *Fusarium oxysporum* trypsin-like protease (SP387) promoter and terminator (WO 96/00787) as regulatory sequences. The plasmid also contained the bar gene as a selectable marker for fungal transformations (de Block et al., 1987, *EMBO Journal* 6:2513–2518).

Figure 5:
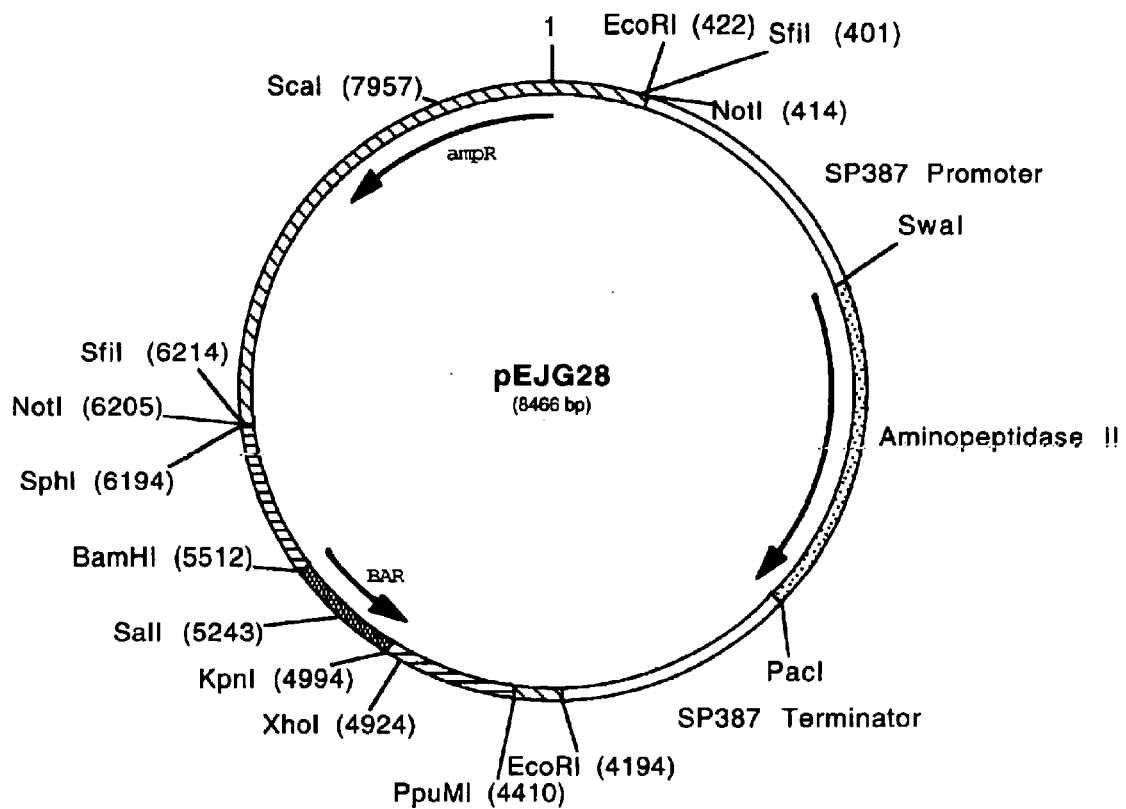
FIG. 5 shows a restriction map of pFJG28.

Fifty picomoles of each of the primers above were used in a PCR reaction containing 70 ng of pEJG18, 1×Pwo Buffer, 5 µl of 10 mM blend of dATP, dTTP, dGTP, and dCTP, and 2.5 units of PwoI. The amplification conditions were one cycle at 94° C. for 2 minutes, 55° C. for 30 seconds, and 72° C. for 1 minute; 9 cycles each at 94° C. for 15 seconds, 55° C. for 30 seconds, and 72° C. for 1 minute; 15 cycles each at 94° C. for 15 seconds, 55° C. for 30 seconds, and 72° C. for 1 minute, with an extension of 20 seconds per cycle; and a final cycle at 94° C. for 15 seconds, 55° C. for 30 seconds, and 72° C. for 7 minutes. The heat block was then held at a 4° C. soak cycle. The amplified 1500 bp DNA fragment was purified by gel electrophoresis and Qiaex II, and then subcloned into pCRII TOPO TA cloning vector (Stratagene, San Diego, Calif.). The pCRII aminopeptidase clone was cut with restriction endonucleases SwaI and PacI (using conditions specified by the manufacturer). The fragment was purified by gel electrophoresis and Qiaex II. The cut fragment was cloned into pDM181 that had been previously cut with SwaI and PacI resulting in the expression plasmid pEJG28 (FIG. 5) in which transcription of the aminopeptidase II gene was under the control of the *Fusarium oxysporum* trypsin-like protease promoter. The plasmid pEJG28 was transformed into *E. coli* ABLE K cells (Stratagene, San Diego, Calif.). The *E. coli* transformant containing the pEJG28 plasmid was isolated and plasmid DNA was prepared according to procedures described by Sambrook et al., 1989, supra.

Example 13

Transformation of Fusarium CC1-3 and Analysis of Transformants

Fusarium strain CC1-3, a highly branched morphological mutant of Fusarium strain A3/5 (ATCC 20334) (Wiebe et al., 1992, *Mycological Research* 96: 555–562; Wiebe et al., 1991, *Mycological Research* 95: 1284–1288; Wiebe et al., 1991, *Mycological Research* 96: 555–562), was grown in a liquid medium containing Vogel's salts, (Vogel, 1964, *Am. Nature* 98: 435–446), 25 mM NaNO$_3$, and 1.5% glucose for 4 days at 28° C. and 150 rpm. Conidia were purified by filtration through 4 layers of cheesecloth and finally through one layer of Miracloth. Conidial suspensions were concentrated by centrifugation. Fifty ml of YPG medium comprised of 1% yeast extract, 2% bactopeptone, and 2% glucose were inoculated with approximately 10$^8$ conidia, and incubated for 14 hours at 24° C. and 150 rpm. Resulting hyphae were trapped on a sterile 0.4 mm filter and washed successively with sterile distilled water and 1.0 M MgSO$_4$. The hyphae were resuspended in 10 ml of NOVOZYM 234™ solution (2–10 mg/ml in 1.0 M MgSO$_4$) and digested for 15–30 minutes at 34° C. with agitation at 80 rpm. NOVOZYM 234™ was obtained from Novo Nordisk A/S, Bagsvaerd, Denmark. Undigested hyphal material was removed from the resulting protoplast suspension by successive filtration through 4 layers of cheesecloth and through Miracloth. Twenty ml of 1 M sorbitol were combined with the protoplast solution. After mixing, the protoplasts were pelleted by centrifugation and washed successively by resuspension and centrifugation in 20 ml of 1 M sorbitol and in 20 ml of STC (0.8 M sorbitol, 0.05 M Tris pH 8.0, 0.05 M CaCl$_2$). The washed protoplasts were resuspended in 4 parts STC and 1 part SPTC (0.8 M sorbitol, 40% PEG 4000, 0.05 M Tris pH 8.0, 0.05 M CaCl$_2$) at a concentration of 5×10$^7$/ml.

One hundred ml of protoplast suspension were added to 10 µg of pEJG28 in polypropylene tubes (17×100 mm), mixed and incubated on ice for 30 minutes. One ml of SPTC was mixed gently into the protoplast suspension and incubation was continued at room temperature for 20 minutes. 12.5 ml of molten solution (cooled to 40° C.) consisting of 1×Vogel's salts, 25 mM NaNO$_3$, 0.8 M sucrose and 1% low melting agarose (Sigma Chemical Company, St. Louis, Mo.) were mixed with the protoplasts and then plated onto an empty 100 mm Petri plate. Incubation was continued at room temperature for 10 to 14 days. After incubation at room temperature for 24 hours, 12.5 ml of the identical medium plus 10 mg of BASTA™ (Hoechst Schering, Rodovre, Denmark) per ml were overlayed onto the Petri plate. BASTA™ was extracted twice with phenol:chloroform:isoamyl alcohol (25:24:1), and once with chloroform:isoamyl alcohol (24:1) before use.

After two weeks, 2 transformants designated #1 and #2 were apparent. A mycelial fragment from the edge of each transformant was transferred to individual wells of a 24 well plate containing Vogel's/BASTA™ medium. The medium contained 25 g of sucrose, 25 g of Noble agar, 20 ml of 50×Vogel's salts (Vogel, 1964, supra), 25 mM NaNO$_3$, and 10 g of BASTA™ per liter. The plate was sealed in a plastic bag to maintain moisture and incubated approximately one week at room temperature.

Example 14

Expression of *Aspergillus oryzae* 1568 Aminopeptidase II Gene in Fusarium

A mycelial fragment from each of the 2 Fusarium CC1-3 transformants described in Example 13 was inoculated into 20 ml of M400Da medium composed of 50 g of maltodextrin, 2.0 g of MgSO$_4$-7H$_2$O, 2.0 g of KH$_2$PO$_4$, 4.0 g of citric acid, 8.0 g of yeast extract, 2.0 g of urea, and 0.5 ml of trace metals solution per liter and incubated for 7 days at 30° C. and 150 rpm. The medium was adjusted to pH 6.0 with 5 N NaOH. The trace metals solution contained 14.3 g of ZnSO4-7H$_2$O, 2.5 g of CuSO$_4$-5H$_2$O, 0.5 g of NiCl$_2$-6H$_2$O, 13.8 g of FeSO$_4$-7H$_2$O, 8.5 g of MnSO$_4$-H$_2$O, and 3.0 g of citric acid per liter. The untransformed host was also run as a control. One ml of culture supernatant was harvested at 7 days and stored and assayed. Aminopeptidase II activity was determined by mixing 10 µl of supernatant with 200 µl of a substrate stock solution containing 2 mg of Leu-paranitroanilide per ml of 50 mN sodium phosphate pH 7.5 buffer and monitoring the change in absorbance at 405 nm over 4 minutes. Both transformants exhibited activity towards Leu-pNA greater than the untransformed control.

The primary Fusarium transformant #2 described in Example 13 was cultivated in 125 ml shake flasks for 5 days at 30° C. in 25 ml of M400Da medium. The whole culture broth was filtered using a double layer of Miracloth. The filtrate was recovered and then frozen at −20° C.

Example 15

Purification of Recombinant *Aspergillus oryzae* 1568 Aminopeptidase II Produced by Fusarium A 20 ml volume of a 5 day Fusarium broth described in Example 14 was filtered through a 0.45 micron syringe filter. The sample was then diluted 8-fold in 20 mM sodium phosphate buffer pH 7.0 buffer. The conductivity and pH of the sample was 3.1 mS and 7.10, respectively. The sample was loaded onto a XK-26 (Pharmacia Biotech AB, Uppsala, Sweden) column containing 60 ml of Q-Sepharose, Big Beads, which had been pre-equilibrated with 20 mM sodium phosphate pH 7.0 buffer. The column was washed until a baseline was reached and then the sample was eluted with a linear gradient from 0–0.5 M NaCl in 20 mM sodium phosphate buffer pH 7.0 over 8.3 column volumes and at a flow rate of 5 ml/min. Fractions were assayed using Leu-pNA as substrate by mixing 10 μl of each fraction with 90 μl of 50 mM sodium phosphate pH 7.5 buffer and 100 μl of a substrate stock solution containing 2 mg of Leu-pNA per ml of 50 mM sodium phosphate pH 7.5 buffer and monitoring the change in absorbance at 405 nm over 4 minutes. All fractions active on Leu-pNA were then pooled, diluted, and concentrated using an Amicon Ultrafiltration unit utilizing a PM 10 membrane.

The concentrated sample was then loaded onto a Mono Q 16/10 (Pharmacia Biotech AB, Uppsala, Sweden) column which had been pre-equilibrated with 20 mM sodium phosphate pH 7.0 buffer. The column was then washed with 0.15 M NaCl. A gradient was performed from 0.15–0.5M NaCl over 10 column volumes at a flow rate of 2 ml/min. Active fractions were then equilibrated in 1.7 M $(NH_4)_2SO_4$ in 50 mM sodium phosphate buffer pH 7.0.

The sample was then loaded onto a Phenyl Superose 5/5 column (Pharmacia Biotech AB, Uppsala, Sweden) which had been pre-equilibrated with 1.7 M $(NH_4)_2SO_4$ in 50 mM sodium phosphate pH 7.0 buffer. The column was washed with 1.7 M $(NH_4)_2SO_4$ in 50 mM sodium phosphate pH. 7.0 buffer until baseline was achieved. The enzyme was eluted with a gradient from 1.7 M to 0 M $(NH4)_2SO_4$ over 30 column volumes at a flow rate of 0.5 ml/min. The flow through had activity on Leu-pNA, as did fractions that were eluted. The enzyme appeared as a series of differentially glycosylated forms based on SDS-PAGE analysis. When the various forms of the enzyme were treated with Endoglycosidase F/N glycosidase F (Boehringer Mannheim, Indianapolis, Ind.), according to the manufacturer's suggested protocol, a single band with a molecular weight of ~58 kDa appeared in all the samples analyzed. The differentially glycosylated forms were then pooled, desalted using 50 mM sodium phosphate buffer pH 7.5, and submitted to biochemical characterization.

Example 16

Characterization of Recombinant *Aspergillus oryzae* 1568 Aminopeptidase II

The purified aminopeptidase II described in Example 11 was used in the following characterization.

Kinetic parameters of the aminopeptidase II were determined for several p-nitroanilides (pNA) including Leu-pNA, Gly-pNA, Ala-pNA, and Pro-pNA (Sigma Chemical Co., St. Louis, Mo., or Bachem, Torrance, Calif.). Stock solutions of 100 mg of each p-nitroanilide per ml of dimethylsulfoxide were diluted with 50 mM potassium phosphate pH 7.0 buffer to concentrations ranging from 0.0064 to 9.56 mM. It should be noted that the solubility of the substrates is not always sufficient to have concentrations comparable to $K_m$, which may result in errors which could be higher than expected normally. The reaction of the aminopeptidase II with the p-nitroanilide was initiated when a 100 μl aliquot of the enzyme solution in 50 mM potassium phosphate pH 7.0 was added to 100 μl of a substrate solution in a microtiter plate well and monitored at 405 nm and 25° C. using a THERMOmax Microplate Reader (Molecular Devices Corp., Sunnyvale, Calif.). Analysis of initial rates of hydrolysis of the p-nitroanilides produced the results shown in Table 1:

TABLE 1

Kinetic parameters of aminopeptidase II at pH 7.0 and 25° C.

| Substrate | $K_m$ (mM) | $V_{max}$ (relative units) |
|---|---|---|
| Leu-pNA | 7 | 6400 |
| Gly-pNA | 0.3 | 1670 |
| Ala-pNA | 11 | 1200 |
| Pro-pNA | 2 | 120 |

The results showed that the aminopeptidase II possesses a substrate specificity where the specificity toward Ala is much worse than toward Gly.

Inhibition of the aminopeptidase II with 1,10-phenanthroline was evaluated using Leu-pNA as substrate at pH 7.5 in 50 mM Tris pH 7.5 buffer where hydrolysis was monitored at 405 nm. A 200 mM solution of 1,10-phenanthroline in methanol was prepared. The inhibition reaction was conducted by mixing 100 μl of 2 mg of Leu-pNA per ml of 50 mM sodium phosphate pH 7.5 solution and 10 μl of the 1,10-phenanthroline solution with 100 μl of aminopeptidase II diluted 5-fold in 50 mM sodium phosphate pH 7.5 buffer. A control was run where 10 μl of 20 mM Tris pH 7.6 buffer was used in place of the 1,10-phenantholine solution.

The results indicated that 1,10-phenanthroline inhibited the aminopeptidase II suggesting that the aninopeptidase II is a metalloprotease. The rate of hydrolysis of Leu-pNA decreased from 285 mOD/minute to 21 mOD/minute in the presence of 1,10-phenanthroline.

The purified aninopeptidase II described in Example 15 was used in the following characterizations.

The pH optimum was determined using Ala-pNA as substrate in the universal buffer composed of 0.125 M citric acid, 0.125 M mono basic sodium phosphate, and 0.125 M boric acid pH was adjusted to 4.5–11 with 10 N NaOH, in 0.5 pH increments. The Ala-pNA substrate was prepared by dissolving 100 mg of Ala-pNA in 1 ml of DMSO and adding 20 μl of the Ala-pNA/DMSO solution to 980 μl of the universal buffer at the various pH values. The assay was initiated by adding a 15 μl aliquot of the aminopeptidase II in 50 mM sodium phosphate pH 7.5 buffer to 200 μl of 2 mg/ml Ala-pNA at the various pH values at ambient temperature. The change in absorbance at 405 nm was monitored for 5 minutes. Autohydrolysis of the substrate as a control was determined by adding 15 μl of 50 mM sodium phosphate pH 7.5 buffer to 200 μl of 2 mg/ml Ala-pNA at the various pH values.

The results shown in Table 2 below demonstrated that the aminopeptidase II possessed activity with Ala-pNA as substrate over the measured pH range 4.91 to 10.91 with optimal activity at pH ~9.5–10. No autohydrolysis of the substrate was observed at pH values of 11 or less.

TABLE 2

| pH | Avg. Activity | Relative Activity |
|---|---|---|
| 4.42 | 0 mOD/min | 0 |
| 4.91 | 2 | 0.006 |
| 5.41 | 7.8 | 0.024 |
| 5.89 | 13.9 | 0.043 |
| 6.40 | 16.37 | 0.051 |
| 6.90 | 23.48 | 0.0727 |
| 7.27 | 41.24 | 0.128 |

TABLE 2-continued

| pH | Avg. Activity | Relative Activity |
|---|---|---|
| 7.59 | 69.15 | 0.214 |
| 8.03 | 145.6 | 0.45 |
| 8.62 | 245.99 | 0.761 |
| 9.25 | 306.97 | 0.95 |
| 9.68 | 323.15 | 1.0 |
| 10.51 | 270.8 | 0.838 |
| 10.95 | 197.86 | 0.612 |

The temperature stability of the aminopeptidase II was determined using the following protocol: 480 µl of 50 mM sodium phosphate buffer pH 7.5 was preincubated at 37°, 45°, 55°, 60°, 65°, 70°, and 75° C. for 30 minutes in a 1.7 ml Eppendorf tube. Then 20 µl of purified aminopeptidase II was added and the sample was then incubated for an additional 20 minutes. The samples were then placed on ice. Once the incubations were completed for all the temperatures, the samples were then assayed for activity using Leu-pNA as substrate.

The assay was performed by mixing 100 µl of the incubation mixtures for the various temperatures with 100 µl of 2 mg/ml Leu-pNA in 50 mM sodium phosphate pH 7.5 buffer at ambient temperature. The absorbance at 405 nm was monitored for 5 minutes.

The results shown in Table 3 demonstrated that the aminopeptidase II retained 90% of its activity after a 20 minute incubation at 60° C., pH 7.5.

TABLE 3

| Temperature (° C.) | Percent activity relative to 37° C. |
|---|---|
| 37 | 100 |
| 45 | 101 |
| 55 | 99 |
| 60 | 90 |
| 65 | 73.7 |
| 70 | 64.6 |
| 75 | 46 |

The kinetic parameters for various aminopeptidase II substrates was determined using the following protocol. Purified aminopeptidase II with an $A_{280}$ of 0.581 was used. Each substrate was dissolved in DMSO to a concentration of 100 mg/ml and then diluted 50 fold in 50 mM sodium phosphate pH7.5 buffer to 2 mg/ml. The substrates included Leu-pNA, Glu-pNA (Bachem, Torrance, Calif.), and Ala-pNA. In a 96 well microtiter plate, 10 µl of purified aminopeptidase II was incubated with each substrate as follows except 50 1 of purified aminopeptidase II was incubated with Glu-pNA, and the absorbance at 405 nm was measured for 4 minutes:

1. 200 µl of 2 mg/ml substrate+0 µl of 50 mM sodium phosphate buffer pH 7.5
2. 100 µl of 2 mg/ml substrate+100 µl of 50 mM sodium phosphate buffer pH 7.5
3. 50 µl of 2 mg/ml substrate+150 µl of 50 mM sodium phosphate buffer pH 7.5
4. 25 µl of 2 mg/ml substrate+175 µl of 50 mM sodium phosphate buffer pH 7.5

A Lineweaver-Burke plot was constructed to determine the $K_m$ and the $k_{cat}$ for each substrate, using an average molecular weight of 97 kDa for the differentially glycosylated forms.

For Leu-pNA, the $K_m$ and $k_{cat}$ were determined to be 5.78 mM and 230.9 $min^{-1}$, respectively.

For Glu-pNA, the $K_m$ and $k_{cat}$ were determined to be 1.17 mM and 8.217 $min^{-1}$, respectively.

For Ala-pNA, the $K_m$ and $k_{cat}$ were determined to be 1.49 mM and 34.638 $min^{31\ 1}$, respectively.

Example 17

Preparation of Protein Hydrolysates with *Aspergillus oryzae* 1568 Aminopeptidase II The purified aminopeptidase II described in Example 11 was tested in degree of hydrolysis assays using soy, wheat gluten, and casein as substrates according to the following procedure.

The degree of hydrolysis (DH) assays were performed at 50° C. for 18 hours as a mini-hydrolysis on a 10 ml scale using soy bean meal tablets, wheat gluten meal tablets, and sodium-caseinate at a 2% concentration adjusted to pH 7, if necessary, with no pH adjustment during hydrolysis. The hydrolysates were inactivated at 85° C. for 3 minutes in a waterbath. The enzymes used were FLAVOURZYME™ and aminopeptidase II. The enzymes were dosed as follows. For soy, 2 LAPUs and 5 LAPUs of aminopeptidase II (recombinant) were added compared to 3 LAPUs of FLAVOURZYME™. For gluten, 2 LAPUs and 5 LAPUs of aminopeptidase II (recombinant) were added compared to 3 LAPUs of FLAVOURZYME™. For casein, 1 and 2 LAPUs of aminopeptidase II (recombinant) were added compared to 3 LAPUs of FLAVOURZYME™. One LAPU (Leucine Amino Peptidase Unit) is the amount of enzyme which decomposes 1 micromole of L-leucine-p-nitroanilide per minute under the following conditions: 26 mM L-leucine-p-nitroanilide in 0.1 M Tris pH 8.0 buffer at 40° C. for 10 minutes. Upon hydrolysis, p-nitroanilide is liberated turning the solution yellow which is monitored 405 nm.

The degree of hydrolysis (DH), as defined as described by Adler-Nissen (1986, *Enzymic Hydrolysis of Food Proteins*, Elsevier Applied Science Publishers), was determined by reaction of the supernatant with OPA (ortho-phtaldialdehyde, Sigma Chemical Co., St. Louis, Mo.) according to the following procedure The hydrolysate was diluted 100-fold into distilled water. Then 120 µl was transferred to 900 µl of OPA reagent. For the OPA reagent, 160 mg of OPA was dissolved in 4 ml of ethanol and transferred to a 200 ml volumetric flask containing a solution of 7.62 g of disodium tetraborate decahydrate, 200 mg of sodium dodecylsulphate, and 176 mg of dithiothreitol and the flask was filled to 200 ml with water. The solution was then shaken well and after 2 minutes exactly, the absorbance at 340 nm was measured and compared to the absorbance of a 0.95 mM L-serine (distilled water) solution after subtraction of the blank value (water reacted with OPA reagent). To determine the true DH, the serine equivalents measured in the hydrolysates were corrected with the factors suggested by Adler-Nissen for the trinitrobenzenesulfonic acid method (Adler-Nissen, 1979, *Agricultural and Food Chemistry* 17: 1256) which gave the same response as the described OPA method. The DH was calculated on the basis of the total amount of protein in the hydrolysis mixture (not on the basis of soluble protein).

A volume of 25 µl of suitably diluted supernatant was mixed with 200 µl of OPA reagent in a microtiter plate well and allowed to react for exactly 2 minutes at 25° C. The absorbance at 340 nm was measured in a microtiter plate reader and compared to the absorbance of a 95 mM L-serine standard solution after subtraction of the blank value (water reacted with OPA-reagent). To determine the true DH, the serine equivalents measured in the supernatants were corrected with the factors suggested by Adler-Nissen for the trinitrobenzenesulfonic acid method (Adler-Nissen, 1979, *Agricultural and Food Chemistry* 17: 1256) which gave the same response as the described OPA method. The degree of hydrolysis was calculated on basis of the total amount of protein in the hydrolysis mixture (not on basis of soluble protein).

For soy, the addition of 2 LAPUs and 5 LAPUs of aminopeptidase II to 3 LAPUs of FLAVOURZYME™ increased absolute DH at least 8% and 10%, respectively, above the samples with 3 LAPUs of FLAVOURZYME™ alone.

For gluten, the addition of 2 LAPUs and 5 LAPUs of aminopeptidase II to 3 LAPUs of FLAVOURZYME™ increased absolute DH 6% and 9%, respectively.

For gelatin, the addition of 2 LAPUs and 5 LAPUs of dipeptide aminopeptidase II to 3 LAPUs of FLAVOURZYME™ increased absolute DH 4.9% and 5.3% respectively.

For casein, the addition of 1 and 2 LAPUs of aminopeptidase II to 3 LAPUs of FLAVOURZYME™ increased absolute DH 7% and 9%, respectively, over the addition of 3 LAPUs of FLAVOURZYME™ alone.

Example 18

Hydrolysis of Soy Protein with *Aspergillus oryzae* Aminopeptidase II

Soy protein was hydrolysed on a 10 ml-scale (mini-hydrolysis) with a start pH of 7.0 and a protein concentration of 2%. The hydrolysis time and temperature were 18 hours and 50° C., respectively. Enzymes were inactivated at 85° C. for 5 minutes and the hydrolysates were centrifuged. The supernatants were analysed for DH using the OPA-method. The DH, as defined as described by Adler-Nissen (1986, *Enzymic Hydrolysis of Food Proteins*, Elsevier Applied Science Publishers), was determined by reaction of the supernatant with OPA (ortho-phtaldialdehyde, Sigma Chemical Co., St. Louis, Mo.). For the OPA reagent, 160 mg of OPA was dissolved in 4 ml of ethanol and transferred to a 200 ml volumetric flask containing a solution of 7.62 g of disodium tetraborate decahydrate, 200 mg of sodium dodecylsulphate, and 176 mg of dithiothreitol and the flask was filled to 200 ml with water. Selected samples were analysed for the content of free amino acids using the PicoTag HPLC method (Waters Associates, Milford, Mass.) according to the manufacturer's instructions.

The dosages of enzymes to each hydrolysis flask containing 200 mg of soy protein are shown in Table 4 below. The aminopeptidase II was produced recombinantly in *Aspergillus oryzae* as described in Example 10 and purified accordingly. The aminopeptidase II solution had an $A_{280}$ of 8.1 and an estimated protein content of 5 mg/ml from amino acid determination.

The results of the DH analysis are presented in Table 4. DH was calculated from the total protein concentration of 2%—not the soluble protein content.

TABLE 4

The DH results for the hydrolysates

|   | FLAVOURZYME ™ 1000 L % | Aminopeptidase II g enz.prot./kg soy protein* | DH % |
|---|---|---|---|
| 1 | 1.5 | 0 | 45.1 |
| 2 | 1.5 | 0.03 | 50.9 |
| 3 | 1.5 | 0.06 | 51.0 |
| 4 | 1.5 | 0.12 | 51.3 |
| 5 | 1.5 | 0.25 | 55.7 |
| 6 | 1.5 | 0.50 | 58.0 |
| 7 | 2.0 | 0 | 51.9 |
| 8 | 6.0 | 0 | 62.8 |
| 9 | 6.0 | 0.03 | 62.9 |
| 10 | 6.0 | 0.06 | 62.9 |
| 11 | 6.0 | 0.12 | 63.6 |
| 12 | 6.0 | 0.25 | 68.5 |
| 13 | 6.0 | 0.50 | 67.8 |
| 14 | 7.0 | 0 | 63.2 |

*The concentration of aminopeptidase II used for this calculation is 5 mg/ml

Table 5 shows the relative % increase in the individual amino acids upon addition of a maximal aminopeptidase II dosage (0.5 g/kg soy protein) to a background dosage of FLAVOURZYME™.

TABLE 5

Relative % increase in free amino acids due to addition of aminopeptidase II

| Aminoacid | 1.5% FLAVOURZYME ™ + Aminopeptidase II | 6% FLAVOURZYME ™ + Aminopeptidase II |
|---|---|---|
| asp | 123.4 | 26.0 |
| glu | 54.2 | 24.5 |
| asn | 115.1 | -7.0 |
| ser | 123.8 | 0.0 |
| gln | 91.7 | 19.8 |
| gly | 145.7 | 22.4 |
| his | 31.9 | 2.8 |
| arg | 24.9 | 6.1 |
| thr | 40.4 | 8.8 |
| ala | 77.4 | 18.5 |
| pro | 87.5 | 59.2 |
| tyr | 51.3 | 10.5 |
| val | 41.4 | 12.7 |
| met | 36.8 | 9.7 |
| cys | 74.4 | 23.2 |
| ile | 24.6 | 13.0 |
| leu | 22.4 | 7.5 |
| phe | 22.8 | 8.0 |
| lys | 49.0 | 10.3 |
| total | 49.1 | 10.6 |
| DH | 28.7 | 8.0 |

The results showed that when aminopeptidase II was added to a low dosage of FLAVOURZYME™ M (1.5%), Gly showed the highest relative increase followed by Ser, Asp, Asn, Pro, Cys, and Ala. When aminopeptidase II was added to a high FLAVOURZYME™ dosage (6%), Pro showed the highest relative increase followed by Asp, Glu, Cys, Gly, and Gln.

Example 19

Increased Protein Solubility and Release of Glutamate by Deamidation

Wheat gluten (WG) was obtained from Cargill (JOB 5141) and deaminated wheat gluten (DWG) was obtained from StaPro Consultancy B. V., Lemdijk 32, 9422 TH Smilde, NL. Suspensions of 8% protein were made by mixing 11 g of gluten with 89 g of water. The pH was adjusted to 6.5 with NaOH. Glutamate/aspartate specific protease (SP446), obtainable as described in WO 91/13554, or lysine/arginine specific protease (SP387) obtainable as described in WO 89/06270, was added to the suspensions. The dosage was 0.01 AU/g protein for SP446 and 0.006 AU/g protein for SP387. FLAVOURZYME™ (an un-specifically acting protease preparation available from Novo Nordisk A/S, Bagsvaerd, Denmark, containing endo- and exo-peptidase activities, and obtained by fermentation of Aspergillus oryzae ) was added to some of the hydrolysates at a dosage of 20 LAPU/g protein.

The hydrolyses were carried out at 50° C. without further pH adjustment for 18 hours. The enzymes were inactivated by heating at 85° C. for 15 minutes. The pH was adjusted to 5 and the hydrolysates were centrifuged. The content of protein and free glutamate in the supernatant was determined.

The protein content was determined by Kjeldahl analysis, using a Kjeldahl factor of 6.25.

The content of free glutamate was determined by use of a glutamate determination kit according to the manufacturer's instructions (Boehringer-Mannheim, Indianapolis, Ind.). The method was adapted for use in microtiter plates.

When comparing wheat gluten (WG) to deaminated wheat gluten (DWG), the results shown in Table 6 demonstrated that deamidation increased the susceptibility of the gluten to specific proteases, such that more protein became soluble. By addition of FLAVOURZYME™ with a specific protease, the release of glutamate was doubled due to deamidation.

TABLE 6

| Hydrolysate | Protein Solubility % | | Glutamate Content mg/l | |
|---|---|---|---|---|
| | WG | DWG | WG | DWG |
| SP446 | 18 | 54 | 0 | 0 |
| SP387 | 35 | 44 | 0 | 0 |
| SP446 + FLAVOURZYME ™ | 34 | 87 | 1000 | 2000 |

Example 20

Enzymatic Deamidation and Release of Glutamate

Peptidoglutaminase II was produced by growing *Bacillus circulans* strain ATCC 21590 in shake flasks (400 ml) containing 200 ml of a medium composed of 1% polypeptone, 0.5% lactose, 0.025% MgSO$_4$-7H$_2$O, 0.005% FeSO$_4$-7H$_2$O, 0.025% KH$_2$PO$_4$, and 17% Na$_2$HPO$_4$-12H$_2$O (pH adjusted to 7.2), at 30° C. for 20 hours with mixing at 270 rpm. The cells were harvested by centrifugation at 4000 rpm in 1 liter flasks. The cells were then frozen.

The purification of peptidoglutaminase II from *Bacillus circulans* was performed at room temperature. The frozen *Bacillus circulans* cells were thawed and suspended in Lysis buffer (50 mM Tris/HCl; 25% (w/v) sucrose; 1 mM EDTA, pH 8.0) until a homogeneous suspension was obtained—100 g wet cells per liter of Lysis buffer. Lysozyme (10 mg/ml) and DNAse I (Sigma DN-25, 10 mg/ml) were dissolved in Lysis buffer. Then 100 ml of lysozyme solution, 10 ml of 1.0 M MgCl$_2$, and 1 ml of DNAse I solution were added per liter of cell suspension. The enzymes were allowed to act for 1 hour.

The suspension was filtered through a Seitz depth filter plate and the filtrate was transferred to a 10 mM KH$_2$PO$_4$/NaOH, pH 8.0 (Buffer A) on a Sephadex G25 column (Pharmacia Biotech AB, Uppsala, Sweden). The enzyme solution was applied to a SOURCE Q column (Pharmacia Biotech AB, Uppsala, Sweden) equilibrated in Buffer A and eluted with a linear NaCl gradient (0→500 mM) in Buffer A. Fractions from the column were analysed for peptidoglutaminase II activity as described below and fractions with activity were pooled. The absorbance of the pooled fractions at 280 nm was 1.78, thus the protein content was estimated to 1.8 mg/ml.

The purity of the protein in the peptidoglutaminase II pool was approximately 25% as judged from a SDS-PAGE gel. Thus, the preparation contained approximately 0.5 mg/ml of pure peptidoglutaminase II.

The peptidoglutaminase activity was determined by measuring the ammonia formed during hydrolysis of γ-carboxyamide of N-tert-Butoxycarbonyl-Gln-Pro (N-t-BOC-Gln-Pro; SIGMA No. B-4403) using the Boehringer-Mannheim kit for ammonia determination (Cat. No. 1112732). In this kit, ammonia is measured by determination of the consumption of NADH by glutamate dehydrogenase, and blanks without the addition of N-t-BOC-Gln-Pro were also applied in order to subtract the effect of other NADH consuming enzymes.

A total of 200 mg of wheat gluten protein was added to 9 ml of boiling water and after cooling, the pH was adjusted to 7.0. Then 250 μl of the peptidoglutaminase II preparation (PEP) described above was added. The glutamate/aspartate specific protease (SP446) described in Example 19 was added in an amount of 0.04 AU/g protein, and FLAVOURZYME™ described in Example 19 was added in an amount of 20 LAPU/g protein.

Hydrolysis was allowed to proceed without pH adjustment for 18 hours at 50° C. Controls without the addition of peptidoglutaminase were also run. The hydrolysates were centrifuged and glutamate was measured as described in Example 19. The DH was determined as described in Example 18.

The results as shown below in Table 7 demonstrated that hydrolysis with the peptidoglutaminase preparation increased the DH as well as the release of glutamate.

TABLE 7

| Hydrolysis | DH % | Glutamate mg/l |
|---|---|---|
| Minus PEP | 40 | 131 |
| Plus PEP | 43 | 171 |

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* DH5α pEJG18 | NRRL B-21677 | Apr. 4, 1997 |

What is claimed is:

1. An isolated secreted polypeptide having aminopeptidase activity with physicochemical properties of (i) a pH optimum in the range of from about pH 7.27 to about pH 10.95 determined at ambient temperature in the presence of Ala-para-nitroanilide; (ii) a temperature stability of 90% or more, relative to initial activity, at pH 7.5 determined after incubation, for 20 minutes at 60° C. In the absence of substrate; (iii) a temperature stability of 64% or more, relative to initial activity, at pH 7.5 determined after incubation for 20 minutes at 70° C. in the absence of substrate; and (iv) an ability to hydrolyze a substrate containing Ala, Arg, Asn, Asp, Cys, Gln, Glu, Gly, His, Ile, Leu, Lys, Phe, Pro, Ser, Thr, Trp, Tyr, or Val at its N-terminus, selected from the group consisting of:
   (a) a polypeptide having an amino acid sequence which has at least 90% identity with the amino acid sequence of amino acids 16 to 496 of SEQ ID NO:2;
   (b) a polypeptide which is encoded by a nucleic acid sequence which hybridizes under medium stringency conditions with (i) the nucleic acid sequence of nucleotides 46 to 1488 of SEQ ID NO:1, or (ii) its full complementary strand, wherein medium stringency conditions are defined as prehybridization and hybridization at 42° C. in 5×SSPE, 0.3% SDS, 200 µg/ml sheared and denatured salmon sperm DNA, and 35% formamide; and (c) a fragment of (a) or (b), wherein the fragment has aminopeptidase activity;

wherein the polypeptide having aminopeptidase activity sequentially removes one amino acid residue at a time from the N-terminus of a peptide, polypeptide, or protein.

2. The polypeptide of claim 1, comprising an amino acid sequence which has at least 90% identity with the amino acid sequence of amino acids 16 to 496 of SEQ ID NO:2.

3. The polypeptide of claim 2, comprising an amino add sequence which has at least 95% identity with the amino acid sequence of amino acids 16 to 496 of SEQ ID NO:2.

4. The polypeptide of claim 3, comprising an amino acid sequence which has at least 97% Identity with the amino acid sequence of amino acids 16 to 496 of SEQ ID NO:2.

5. The polypeptide of claim 1, comprising the amino acid sequence of amino acids 16 to 496 of SEQ ID NO:2 or a fragment of contiguous amino acids of amino acids 16 to 496 of SEQ ID NO:2 wherein the fragment has aminopeptidase activity.

6. The polypeptide of claim 2, which is obtained from an Aspergillus strain.

7. The polypeptide of claim 6, which is obtained from an *Aspergillus oryzae* strain.

8. The polypeptide of claim 1, which is encoded by a nucleic acid sequence which hybridizes under medium stringency conditions with the nucleic acid sequence of nucleotides 46 to 1488 of SEQ ID NO:1 or its full complementary strand, wherein medium stringency conditions are defined as prehybridization and hybridization at 42° C. in 5×SSPE, 0.3% SDS, 200 µg/ml sheared and denatured salmon sperm DNA. and 35% formamide.

9. The polypeptide of claim 8, which is obtained from an Aspergillus strain.

10. The polypeptide of claim 9, which is obtained from an *Aspergillus oryzae* strain.

11. The polypeptide of claim 1, which is encoded by a nucleic acid sequence which hybridizes under high stringency conditions with the nucleic acid sequence of nucleotides 46 to 1488 of SEQ ID NO:1 or its full complementary strand, wherein high stringency conditions are defined as prehybridization and hybridization at 42° C. in 5×SSPE, 0.3% SDS, 200 µg/ml sheared and denatured salmon sperm DNA, and 50% formamide.

12. The polypeptide of claim 3, which is obtained from an Aspergillus strain.

13. The polypeptide of claim 12, which is obtained from an *Aspergillus oryzae* strain.

14. The polypeptide of claim 1, which is encoded by the nucleic acid sequence contained in plasmid pEJG18 which is contained in *E. coli* NRRL B-21677.

15. The polypeptide of claim 1, wherein the polypeptide hydrolyzes a substrate containing Ala, Glu, Gly, or Pro at it N-terminus.

16. A method for producing the isolated secreted polypeptide of claim 1 comprising (a) cultivating a microbial strain, which in its wild-type form produces the polypeptide, in a medium under conditions suitable for production of the polypeptide; and (b) isolating the polypeptide from the medium.

17. A composition comprising the isolated secreted polypeptide of claim 1 and a suitable carrier.

18. The composition of claim 17, wherein the polypeptide comprises an amino acid sequence which has at least 90% identity with the amino acid sequence of amino acids 16 to 496 of SEQ ID NO:2.

19. The composition of claim 18, wherein the polypeptide comprises an. amino acid sequence which has at least 95% identity with the amino acid sequence of amino acids 16 to 496 of SEQ ID NO:2.

20. The composition of claim 18, wherein the polypeptide comprises an amino acid sequence which has at least 97% identity with the amino acid sequence of amino acids 16 to 496 of SEQ ID NO:2.

21. The composition of claim 17, wherein the polypeptide comprises the amino acid sequence of amino acids 16 to 496 of SEQ ID NO:2 or a fragment of contiguous amino acids of amino acids 16 to 496 of SEQ ID NO:2 wherein the fragment has aminopeptidase activity.

22. The composition of claim 21, wherein the polypeptide is obtained from an Aspergillus strain.

23. The composition of claim 22, wherein the polypeptide is obtained from an *Aspergillus oryzae* strain.

24. The composition of claim 17, wherein the polypeptide is encoded by a nucleic acid sequence which hybridizes under medium stringency conditions with the nucleic acid sequence of nucleotides 46 to 1488 of SEQ ID NO:1, or its full complementary strand, wherein medium stringency conditions are defined as prehybridzation and hybridization at 42° C. in 5×SSPE, 0.3% SDS, 200 µg/ml sheared and denatured salmon sperm DNA, and 35% formamide.

25. The composition of claim 24, wherein the polypeptide is obtained from an Aspergillus strain.

26. The composition of claim 25, wherein the polypeptide is obtained from an *Aspergillus oryzae* strain.

27. The composition of claim 17, wherein the polypeptide Is encoded by a nucleic acid sequence which hybridizes under high stringency conditions with the nucleic acid sequence of nucleotides 46 to 1488 of SEQ ID NO:1, or its full complementary strand, wherein high stringency conditions are defined as prehybridization and hybridization at 42° C. in 5×SSPE, 0.3% SDS, 200 µg/ml sheared and denatured salmon sperm DNA, and 50% formamide.

28. The composition of claim 27, wherein the polypeptide is obtained from an Aspergillus strain.

29. The composition of claim 28, wherein the polypeptide Is obtained from an *Aspergillus oryzae* strain.

30. The composition of claim 17, wherein the polypeptide is encoded by the nucleic acid sequence contained in plasmid pEJG18 contained in *E. coli* NRRL B-21677.

* * * * *